United States Patent
Ji et al.

(10) Patent No.: US 12,109,273 B2
(45) Date of Patent: *Oct. 8, 2024

(54) PROCESS FOR PREPARING ANTIBODY-DRUG CONJUGATES WITH IMPROVED HOMOGENEITY

(71) Applicant: WUXI XDC SINGAPORE PRIVATE LIMITED, Singapore (SG)

(72) Inventors: Ao Ji, Shanghai (CN); Chuchu Sun, Shanghai (CN); Wenxu He, Shanghai (CN)

(73) Assignee: WUXI XDC SINGAPORE PRIVATE LIMITED, Singapore (SG)

(*) Notice: Subject to any disclaimer, the term of this patent is extended or adjusted under 35 U.S.C. 154(b) by 302 days.

This patent is subject to a terminal disclaimer.

(21) Appl. No.: 17/410,574

(22) Filed: Aug. 24, 2021

(65) Prior Publication Data

US 2021/0379193 A1    Dec. 9, 2021

Related U.S. Application Data

(63) Continuation of application No. 17/430,494, filed as application No. PCT/CN2020/075162 on Feb. 14, 2020, now Pat. No. 11,478,553.

(30) Foreign Application Priority Data

Feb. 15, 2019 (WO) ................ PCT/CN2019/075217

(51) Int. Cl.
| A61K 47/68 | (2017.01) |
| A61K 31/40 | (2006.01) |
| C07K 16/28 | (2006.01) |
| C07K 16/32 | (2006.01) |

(52) U.S. Cl.
CPC .......... *A61K 47/6803* (2017.08); *A61K 31/40* (2013.01); *C07K 16/2863* (2013.01); *C07K 16/2887* (2013.01); *C07K 16/32* (2013.01); *C07K 2317/24* (2013.01); *C07K 2317/55* (2013.01)

(58) Field of Classification Search
None
See application file for complete search history.

(56) References Cited

U.S. PATENT DOCUMENTS

| 4,816,397 | A | 3/1989 | Boss et al. |
| 4,816,567 | A | 3/1989 | Cabilly et al. |
| 5,225,539 | A | 7/1993 | Winter |
| 5,500,362 | A | 3/1996 | Robinson et al. |
| 5,585,089 | A | 12/1996 | Queen et al. |
| 5,770,429 | A | 6/1998 | Lonberg et al. |
| 5,807,715 | A | 9/1998 | Morrison et al. |
| 5,821,337 | A | 10/1998 | Carter et al. |
| 6,075,181 | A | 6/2000 | Kucherlapati et al. |
| 6,150,584 | A | 11/2000 | Kucherlapati et al. |
| 7,041,870 | B2 | 5/2006 | Tomizuka et al. |
| 7,189,826 | B2 | 3/2007 | Rodman |
| 7,521,541 | B2 | 4/2009 | Eigenbrot et al. |
| 7,659,241 | B2 | 2/2010 | Senter et al. |
| 7,723,485 | B2 | 5/2010 | Junutula et al. |
| 7,837,908 | B2 | 11/2010 | Tsuchida |
| 8,394,607 | B2 | 3/2013 | Ebens et al. |
| 9,517,276 | B2 | 12/2016 | Lowman et al. |
| 10,035,853 | B2 | 7/2018 | Arathoon et al. |
| 10,464,997 | B2 | 11/2019 | Meyer |
| 10,603,388 | B2 | 3/2020 | Payne et al. |
| 10,653,794 | B2 | 5/2020 | Zhong et al. |
| 10,744,204 | B2 | 8/2020 | Gao et al. |
| 10,814,009 | B2 | 10/2020 | Coumans et al. |
| 11,478,553 | B2 * | 10/2022 | Ji ........................ C07K 16/32 |
| 2004/0229310 | A1 | 11/2004 | Simmons |
| 2005/0048572 | A1 | 3/2005 | Reilly et al. |
| 2007/0061900 | A1 | 3/2007 | Murphy et al. |
| 2012/0121615 | A1 | 5/2012 | Flygare et al. |
| 2017/0072067 | A1 | 3/2017 | Lowman et al. |
| 2017/0190766 | A1 | 7/2017 | Perlroth et al. |
| 2018/0147292 | A1 | 5/2018 | Noguchi et al. |
| 2019/0365917 | A1 | 12/2019 | Payne et al. |

(Continued)

FOREIGN PATENT DOCUMENTS

| CN | 104936621 | 9/2015 |
| CN | 105849126 | 8/2016 |

(Continued)

OTHER PUBLICATIONS

Strop et al., Chemistry and Biology 20: 161-167 (Year: 2013).*
Piche-Nicholas et al., MABS 10(1): 81-94 (Year: 2018).*
Edwards et al., J Mol Biol. 334(1): 103-118 (Year: 2003).*
Lloyd et al. Protein Engineering, Design & Selection 22:159-168 (Year: 2009).*
Briney et al., Nature 566: 393 (Year: 2019).*
PCT International Search Report and Written Opinion, PCT Application No. PCT/CN2020/075162, filed Feb. 14, 2020, mailed on May 11, 2020, 14 pages.
Mcauley et al., "Contributions of a disulfide bond to the structure, stability, and dimerization of human IgG1 antibody CH3 domain," Protein Science, 2008, 17:95-106.

(Continued)

*Primary Examiner* — Phuong Huynh
(74) *Attorney, Agent, or Firm* — Fish & Richardson P.C.

(57) ABSTRACT

The present disclosure relates to an applicable bio-conjugation process for preparing antibody-drug conjugates (ADCs) with improved homogeneity. As compared with conventional conjugation process, the homogeneity of antibody-drug conjugate (ADC) products generated from the bio-conjugation process can be dramatically improved. Specifically, in the ADCs prepared by the process of the present disclosure, the content of D0+D8 is less than 10 wt % and the content of D6 is less than 10 wt %. Moreover, the content of D4 is generally more than 65 wt %, for example, more than 70 wt %, and more than 77 wt %, while the content of D4 is normally less than 40 wt % in the ADCs prepared by conventional conjugation processes.

19 Claims, 3 Drawing Sheets

(56) References Cited

U.S. PATENT DOCUMENTS

| | | |
|---|---|---|
| 2020/0230256 A1 | 7/2020 | Zhong et al. |
| 2020/0276331 A1 | 9/2020 | Coumans |
| 2020/0405874 A1 | 12/2020 | Hildebrand et al. |
| 2021/0379193 A1 | 12/2021 | Ji et al. |

FOREIGN PATENT DOCUMENTS

| | | |
|---|---|---|
| CN | 106163559 | 11/2016 |
| CN | 106459200 | 2/2017 |
| CN | 107922477 | 4/2018 |
| EP | 0125023 | 11/1984 |
| EP | 0171496 | 2/1986 |
| EP | 0173494 | 3/1986 |
| EP | 0184187 | 6/1986 |
| EP | 3311846 | 4/2018 |
| EP | 3315512 | 5/2018 |
| WO | WO 1986001533 | 3/1986 |
| WO | WO 1987002671 | 5/1987 |
| WO | WO 2005084390 | 9/2005 |
| WO | WO 2006065533 | 6/2006 |
| WO | WO 2008141044 | 11/2008 |
| WO | WO 2009052249 | 4/2009 |
| WO | WO 2011069104 | 6/2011 |
| WO | WO 2013190292 | 12/2013 |
| WO | WO 2014197612 | 12/2014 |
| WO | WO 2015031698 | 3/2015 |
| WO | WO 2015123265 | 8/2015 |
| WO | WO 2015157595 | 10/2015 |
| WO | WO 2016036861 | 3/2016 |
| WO | WO 2016141585 | 9/2016 |
| WO | WO 2017002776 | 1/2017 |
| WO | WO 2017025897 | 2/2017 |
| WO | WO 2017068511 | 4/2017 |
| WO | WO 2017117464 | 7/2017 |
| WO | WO 2017137628 | 8/2017 |
| WO | WO 2018112253 | 6/2018 |
| WO | WO 2018215427 | 11/2018 |
| WO | WO 2020191306 | 9/2020 |

OTHER PUBLICATIONS

Extended European Search Report in European Appln. No. 20755234.0, dated Mar. 6, 2023, 11 pages.

Al-Lazikani et al., "Standard conformations for the canonical structures of immunoglobulins," J. Mol. Biol., Nov. 7, 1997, 273(4):927-948.

Alley et al., "Controlling the location of drug attachment in antibody-drug conjugates," Proceedings of the AACR, Apr. 2004, 45(7):Abstract 627, 3 pages.

Better et al., "*Escherichia coli* Secretion of an Active Chimeric Antibody Fragment," Science, May 20, 1988, 240(4855):1041-1043.

Chari et al., "Immunoconjugates containing novel maytansinoids: promising anticancer drugs," Cancer Research, Jan. 1992, 52(1):127-131.

Chothia et al., "Canonical structures for the hypervariable regions of immunoglobulins," J. Mol. Biol., Aug. 20, 1987, 196(4):901-917.

Chothia et al., "Conformations of immunoglobulin hypervariable regions," Nature, Dec. 28, 1989, 342(6252):877-883.

Chothia et al., "Domain association in immunoglobulin molecules: The packing of variable domains," J. Mol. Biol., Dec. 5, 1985, 186(3):651-663.

Clackson et al., "Making antibody fragments using phage display libraries," Nature, Aug. 15, 1991, 352:624-628.

Clynes et al., "Fc receptors are required in passive and active immunity to melanoma," Proc. Natl. Acad. Sci. USA, Jan. 20, 1998, 95(2):652-656.

DiJoseph et al., "Antibody-targeted chemotherapy with CMC-544:A CD22-targeted immunoconjugate of calicheamicin for the treatment of B-lymphoid malignancies," Blood, Mar. 1, 2004, 103(5):1807-1814.

Dornan et al., "Therapeutic potential of an anti-CD79b antibody-drug conjugate, anti-CD79b-vc-MMAE, for the treatment of non-Hodgkin lymphoma," Blood, Sep. 24, 2009, 114(13):2721-2729.

Flatman et al., "Process analytics for purification of monoclonal antibodies," J. Chromatogr. B, Mar. 15, 2007, 848(1):79-87.

Francisco et al., "Agonistic properties and in vivo antitumor activity of the anti-CD-40 antibody, SGN-14" Cancer Res., Jun. 2000, 60(12):3225-3231.

Frankel et al., "Cell surface receptor-targeted therapy of acute myeloid leukemia: a review," Cancer Biother. Radiopharm., Oct. 2000, 15(5):459-476.

Gazzano-Santoro et al., "A non-radioactive complement-dependent cytotoxicity assay for anti-CD20 monoclonal antibody," J. Immunol. Methods, Mar. 28, 1997, 202(2):163-171.

Hamblett et al., "Effect of drug loading on the pharmacology, pharmacokinetics, and toxicity of an anti-CD30 antibody-drug conjugate," Proceedings of the AACR, Mar. 2004, 45:Abstract 624, 3 pages.

Hamblett et al., "Effects of Drug Loading on the Antitumor Activity of a Monoclonal Antibody Drug Conjugate," Clin. Cancer Res., Oct. 2004, 10:7063-7070.

Jiang et al., "HER2-targeted antibody drug conjugates for ovarian cancer therapy," European J. of Pharmaceutical Sciences, Oct. 10, 2016, 93:274-286.

Jones et al., "Replacing the complementarity-determining regions in a human antibody with those from a mouse," Nature, 1986, 321:552-525.

Junutula et al., "Site-specific conjugation of a cytotoxic drug to an antibody improves the therapeutic index," Nature Biotech., Jul. 20, 2008, 26(8):925-932.

Kohler et al., "Continuous cultures of fused cells secreting antibody of predefined specificity," Nature, Aug. 7, 1975, 256:495-497.

Kozbor et al., "The production of monoclonal antibodies from human lymphocytes," Immunology Today, Mar. 1983, 4(3):72-79.

Li et al., "Human antibodies for immunotherapy development generated via a human B cell hybridoma technology," Proc. Natl. Acad. Sci. USA, Mar. 7, 2006, 103(10):3557-3562.

Liu et al., "Chimeric mouse-human IgG1 antibody that can mediate lysis of cancer cells," Proc. Natl. Acad. Sci. USA, May 1, 1987, 84(10):3439-3443.

Lonberg, "Human antibodies from transgenic animals," Nat. Biotech., Sep. 7, 2005, 23:1117-1125.

Lund et al., "Expression and characterization of truncated forms of humanized L243 IgG1," Eur. J. Biochem., Dec. 2000, 267(24):7246-7256.

Marks et al., "By-passing immunization: Human antibodies from V-gene libraries displayed on phage," J. Mol. Biol., Dec. 5, 1991, 222(3):581-597.

McDonagh et al., "Engineered antibody-drug conjugates with defined sites and stoichiometries of drug attachment," Prot. Engr. Design & Selection, Jul. 2006, 19(7):299-307.

Morrison et al., "Chimeric human antibody molecules: mouse antigen-binding domains with human constant region domains," Proc. Natl. Acad. Sci. USA, Nov. 1, 1984, 81(21):6851-6855.

Morrison, "Transfectomas Provide Novel Chimeric Antibodies," Science, Sep. 20, 1985, 229(4719):1202-1207.

Nishimura et al., "Recombinant Human-Mouse Chimeric Monoclonal Antibody Specific for Common Acute Lymphocytic Leukemia Antigen," Cancer Res., Feb. 1987, 47:999-1005.

Olafsen et al., "Characterization of engineered anti-p185HER-2 (scFv-CH3)2 antibody fragments (minibodies) for tumor targeting," Protein Eng. Design & Sel., Apr. 2004, 17(4):315-323.

Olsson et al., "Human-human monoclonal antibody-producing hybridomas: Technical aspects," Meth. Enzymol., 1983, 92:3-16.

Ravetch et al., "Fc Receptors," Annu. Rev. Immunol., 1991, 9:457-492.

Roux et al., "Comparisons of the Ability of Human IgG3 Hinge Mutants, IgM, IgE, and IgA2, to Form Small Immune Complexes: A Role for Flexibility and Geometry," J. Immunol., Oct. 15, 1998, 161(8):4083-4090.

Shaw et al., "Mouse/Human Chimeric Antibodies to a Tumor-Associated Antigen: Biologic Activity of the Four Human IgG Subclasses," J. Natl. Cancer Inst., Dec. 7, 1988, 80:1553-1559.

(56) References Cited

OTHER PUBLICATIONS

Sochaj et al., "Current methods for the synthesis of homogeneous antibody-drug conjugates," Nature Biotechnology Advances, Nov. 1, 2015, 33:775-784, 10 pages.

Stebbing et al., "Herceptin (trastuzamab) in advanced breast cancer," Cancer Treat Rev., Aug. 2000, 26(4):287-290.

Sun et al., "Chimeric antibody with human constant regions and mouse variable regions directed against carcinoma-associated antigen 17-1A," Proc. Natl. Acad. Sci. USA, Jan. 1, 1987, 84(1):214-218.

Teng et al., "Construction and testing of mouse—human heteromyelomas for human monoclonal antibody production," Proc. Natl. Acad. Sci., USA, 1983, 80(23):7308-7312.

Trail et al., "Effect of Linker Variation on the Stability, Potency, and Efficacy of Carcinoma-reactive BR64-Doxorubicin Immunoconjugates," Cancer Research, 1997, 57(1):100-105.

Verhoeyen et al., "Reshaping Human Antibodies: Grafting an Antilysozyme Activity," Science, Mar. 25, 1988, 239:1534-1536.

Vollmers et al., "Death by Stress: Natural IgM-Induced Apoptosis," Methods and Findings in Experimental and Clinical Pharmacology, 2005, 27(3):185-191, 7 pages.

Wood et al., "The synthesis and in vivo assembly of functional antibodies in yeast," Nature, 1985, 314:446-449.

Zhang et al., "Complete disulfide bond assignment of a recombinant immunoglobulin G4 monoclonal antibody," Anal. Biochem., Dec. 1, 2002, 311(1):1-9.

Erlandsson et al., "Metallic Zinc Reduction of Disulfide Bonds between Cysteine Residues in Peptides and Proteins," International Journal of Peptide Research and Therapeutics, 2005, 11(4):261-265.

Hagihara et al., "Engineering disulfide bonds within an antibody," Biochimica et Biophysica Acta, 2014, 1844:2016-2023.

Liu et al., "Disulfide bond structures of IgG molecules, Structural variations, chemical modifications and possible impacts to stability and biological function," mAbs, Jan.-Feb. 2012, 4:1, pp. 17-23.

Yao et al., "Methods to Design and Synthesize Antibody-Drug Conjugates (ADCs)," International Journal of Molecular Sciences, 2016, 17(194):1-16.

* cited by examiner

PROCESS FOR PREPARING ANTIBODY-DRUG CONJUGATES WITH IMPROVED HOMOGENEITY

CROSS-REFERENCE TO RELATED APPLICATIONS

The present application is a continuation of U.S. application Ser. No. 17/430,494, filed Aug. 12, 2021, which is a National Phase Application under 35 U.S.C. § 371 of PCT/CN2020/075162, filed on Feb. 14, 2020, which claims the benefit of PCT/CN2019/075217, filed Feb. 15, 2019. The contents of the aforementioned application are hereby incorporated by reference.

FIELD OF INVENTION

The present disclosure relates to a process for preparing antibody-drug conjugates (ADCs). Specifically, the present disclosure relates to a bio-conjugation process for preparing antibody-drug conjugates (ADCs) with improved homogeneity.

BACKGROUND OF INVENTION

The specificity of antibodies for specific antigens on the surface of target cells and molecules has led to their extensive use as carriers of a variety of diagnostic and therapeutic agents. For example, antibodies conjugated to labels and reporter groups such as fluorophores, radioisotopes and enzymes find use in labelling and imaging applications, while conjugation to cytotoxic agents and chemotherapy drugs allows targeted delivery of such agents to specific tissues or structures, for example particular cell types or growth factors, minimizing the impact on normal, healthy tissue and significantly reducing the side effects associated with chemotherapy treatments. Antibody-drug conjugates (ADC) are conjugate of an antibody and a drug, and have extensive potential therapeutic applications in several disease areas, particularly in cancer, and become a novel targeted drug for disease treatment. ADC contains an antibody for targeting, a connector or linker for drug attachment and a high potent payload (e.g., a drug) as effector. Since the approvals of Adcetris in 2011 and Kadcyla in 2013 by US FDA, ADC drug development has widely spread for the treatment of cancer.

Specifically, antibody-drug conjugates (ADCs) are an important class of highly potent biopharmaceutical drugs designed as a targeted therapy for the treatment of subjects with cancer. ADCs are complex molecules composed of an antibody linked to a biologically active cytotoxic (e.g., anticancer) drug. They combine ideal properties of both antibodies and cytotoxic drugs by targeting potent cytotoxic drugs to antigen-expressing cells, thereby enhancing their targeted cytotoxicactivity. In contrast to traditional chemotherapeutic drugs, antibody-drug conjugates target only cancer cells so that healthy cells are less severely affected (Dijoseph, J F; Armellino, D C; Boghaert, E R; Khandke, K; Dougher, M M; Sridharan, L; Kunz, A; Hamann, P R; Gorovits, B; Udata, C; Moran, J K; Popplewell, A G; Stephens, S; Frost, P; Damle, N K (2004). "Antibody-targeted chemotherapy with CMC-544: A CD22-targeted immunoconjugate of calicheamicin for the treatment of B-lymphoid malignancies". Blood. 103 (5): 1807-14, and Mullard, Asher (2013). "Maturing antibody-drug conjugate pipeline hits 30". Nature Reviews Drug Discovery. 12 (5): 329-32).

In developing antibody-drug conjugates, an anticancer drug is coupled to an antibody that specifically targets a certain tumor marker (e.g. a protein that, ideally, is only to be found in or on tumor cells). Antibodies track these proteins down in the body and attach themselves to the surface of cancer cells. The biochemical reaction between the antibody and the target protein (i.e., antigen) triggers a signal in the tumor cell, which then absorbs or internalizes the antibody together with the cytotoxin. After the ADC is internalized, the cytotoxic drug is released and kills the tumor cells (Chari, Ravi V. J.; Martell, Bridget A.; Gross, Jonathan L.; Cook, Sherrilyn B.; Shah, Sudhir A.; BlAttler, Walter A.; McKenzie, Sara J.; Goldmacher, Victor S. (1992). "Immunoconjugates containing novel maytansinoids: promising anticancer drugs". Cancer Research. 52 (1): 127-31.. Due to this targeting, ideally the ADC has lower side effects and gives a wider therapeutic window than other chemotherapeutic agents.

For drug attachment, functional groups with high reactivity and stability on both antibody and linker-payload (i.e., linker-drug) were used for the coupling, to form stable covalent bonds. Conventional means of attaching, i.e., covalent bonding of a drug moiety to an antibody via a linker, generally leads to a heterogeneous mixture of molecules where the drug moieties are attached at several sites on the antibody. For example, cytotoxic drugs have typically been conjugated to antibodies through the often-numerous lysine residues of an antibody, generating a heterogeneous antibody-drug conjugate mixture.

For example, antibody-drug conjugates are usually produced by two conventional chemical strategies, Lysine based conjugation and Cysteine from the reduction of interchain sulfide bonds based conjugation. For the reaction of primary amine group on Lysine residue, the most widely used connector on linker-payload is the NHS ester (i.e., N-hydroxysuccinimide). But the application of NHS ester in antibody-drug conjugate production is limited by its inherent properties, for instance, the reaction between NHS ester and primary amine is very slow under acidic conditions, so the conjugation needs to be performed in the buffer with high pH value (i.e., >7.0), which is not friendly to antibody sometimes, and the NHS is prone to hydrolysis under basic conditions, which makes the purification and identification of free drug after conjugation more complicated. Also, due to the low reactivity of NHS ester to primary amine on antibody, the reaction needs to be carried out with high temperature (i.e., 22° C.). Even more, due to the low solubility, more organic solvent is required for linker-payload prepared by NHS ester (i.e., SMCC-DM1) to be fully dissolved in the reaction systems, which increases the risk of aggregation of antibody. For Cysteine from the reduction of interchain sulfide bonds based conjugation, it comprises a step of opening inter-chain disulfide bonds in the presence of various reductants, such TCEP, DTT and so on, followed by nucleophilic reaction of thiol groups. In this conjugation process, antibody-drug conjugates are typically formed by conjugating one or more antibody cysteine thiol groups to one or more linker moieties bound to a drug thereby forming an antibody-linker-drug complex. Cysteine thiols are reactive at neutral pH, unlike most amines which are protonated and less nucleophilic near pH 7. Since free thiol (RSH, sulfhydryl) groups are relatively reactive, proteins with cysteine residues often exist in their oxidized form as disulfide-linked oligomers or have internally bridged disulfide groups. Antibody cysteine thiol groups are generally more reactive, i.e. more nucleophilic, towards electrophilic conjugation reagents than antibody amine or hydroxyl groups. Engineering in cysteine thiol groups by the mutation of various amino acid residues of a protein to cysteine amino acids is potentially problematic, particularly in the case of unpaired (free Cys) residues or those which are relatively accessible for reaction or oxidation. In concentrated solutions of the protein, whether in the periplasm of *E. coli*, culture supernatants, or partially or completely purified protein, unpaired Cys residues on the surface of the protein can pair and oxidize to form intermolecular disulfides, and hence protein dimers or multimers form. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys groups are unavailable for active site participation and interactions. Furthermore, the protein may be rendered inactive or non-specific, by misfolding or loss of tertiary structure (Zhang et al. (2002) Anal. Biochem. 311: 1-9).

It is of great importance to develop new ADCs as therapeutic agents. However, the conventional conjugation processes always result in a heterogeneous mixture of molecules where the drug moieties are attached at several sites on the antibody. Depending on reaction conditions, the heterogeneous mixture typically contains a distribution of antibodies with from 0 to about 8, or more, attached drug moieties. In addition, within each subgroup of conjugates with a particular integer ratio of drug moieties to a single antibody, there is a potentially heterogeneous mixture where the drug moiety is attached at various sites on the antibody. Analytical and preparative methods are inadequate to separate and characterize the antibody-drug conjugate species molecules within the heterogeneous mixture resulting from a conjugation reaction. The heterogeneous mixture is so complex that it is difficult and expensive to characterize and purify. Each conjugation product in such a mixture potentially has different pharmacokinetic, distribution, toxicity and efficacy profiles, and non-specific conjugation also frequently results in impaired antibody function. Antibodies are large, complex and structurally diverse biomolecules, often with many reactive functional groups. Antibody reactivity with linker reagents and drug-linker intermediates are dependent on factors such as pH, concentration, salt concentration, and co-solvents. Furthermore, the multistep conjugation process may be nonreproducible due to difficulties in controlling the reaction conditions and characterizing reactants and intermediates.

Antibody-drug conjugates are typically formed by conjugating one or more antibody cysteine thiol groups to one or more linker moieties bound to a drug thereby forming an antibody-linker-drug complex. Cysteine thiols are reactive at neutral pH, unlike most amines which are protonated and less nucleophilic near pH 7. Since free thiol (RSH, sulfhydryl) groups are relatively reactive, proteins with cysteine residues often exist in their oxidized form as disulfide-linked oligomers or have internally bridged disulfide groups. Antibody cysteine thiol groups are generally more reactive, i.e. more nucleophilic, towards electrophilic conjugation reagents than antibody amine or hydroxyl groups. Engineering in cysteine thiol groups by the mutation of various amino acid residues of a protein to cysteine amino acids is potentially problematic, particularly in the case of unpaired (free Cys) residues or those which are relatively accessible for reaction or oxidation. In concentrated solutions of the protein, whether in the periplasm of *E. coli*, culture supernatants, or partially or completely purified protein, unpaired Cys residues on the surface of the protein can pair and oxidize to form intermolecular disulfides, and hence protein dimers or multimers. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys groups are unavailable for active site participation and interactions. Furthermore, the protein may be rendered inactive or non-specific, by misfolding or loss of tertiary structure (Zhang et al. (2002) Anal. Biochem. 311: 1-9).

Furthermore, the number of drugs coupling to a single antibody molecule is an important factor for the efficacy and safety of the resultant ADC. For example, in the conjugation process based on native inter-chain disulfide bond reduction, the inter-chain S—S bonds are more accessible to solvents than other disulfide bonds. Therefore, the inter-chain disulfide bonds can be used as the binding sites for coupling a drug (or a drug-linker) to an antibody. In general, one therapeutic antibody molecule belonging to IgG1 or IgG4 subclass has 4 inter-chain S—S bonds, each of which is formed with two —SH groups, and thus, the number of drugs coupling to a single antibody molecule is 2, 4, 6 or 8. If the number of drugs coupling to a single antibody molecule is 0, the product is referred to as D0. Accordingly, D2 refers to the ADC in which two drug molecules are coupled to one single antibody molecule, where two drug molecules may be coupled to —SH groups generated by reduction of S—S bonds between heavy and light chains, or may be coupled to —SH groups generated by reduction of S—S bonds between heavy and heavy chains. D4 refers to the ADC in which four drug molecules are coupled to one single antibody molecule. D6 refers to the ADC in which six drug molecules are coupled to one single antibody molecule. And D8 refers to the ADC in which eight drug molecules are coupled to one single antibody molecule, i.e., all the four S—S bonds in one antibody molecule are reduced to eight —SH groups and each —SH group attaches one drug molecule. In general, the heterogeneous mixture of ADC molecules generated by conventional conjugation processes is a mixture of D0, D2, D4, D6 and D8. It is well known in the art that heterogeneous ADC products are generally instable and have low immunogenicity. Among them, D0 has no ADC efficacy, and due to their hydrophobicity induced from payload (i.e., drug) molecules, D6+D8 is considered to be the reason of instability and low immunogenicity. Although antibody-drug conjugate potency in vitro has been shown to be directly dependent on drug loading (Hamblett K J, et al., Clin Cancer Res. 2004 Oct. 15; 10(20):7063-70), in-vivo antitumor activity of antibody-drug conjugates with four drugs per molecule (D4) was comparable with conjugates with eight drugs per molecule (D8) at equal mAb doses, even though the conjugates contained half the amount of drug per mAb. Drug-loading also affected plasma clearance, with the D8 conjugate being cleared 3-fold faster than the D4 conjugate and 5-fold faster than a D2 conjugate. In general, the level of D4 represents the homogeneity of the antibody-drug conjugates. That is, if the content of D4 is high in the mixture, the ADCs are considered to have a high homogeneity. Antibody-drug conjugates with improved homogeneity provide benefits in therapy, for example a higher therapeutic index, improving efficacy and reducing toxicity of the drug. Homogeneous antibody conjugates also provide more accurate and consistent measurements in diagnostic and imaging applications. So, novel processes for preparing ADCs with high homogeneity are highly desirable and long-term pursuit.

It is important for optimized efficacy and to ensure dose to dose consistency that the number of conjugated drug moieties per antibody is the same, and that each moiety is specifically conjugated to the same amino acid residue in each antibody. Accordingly, a number of methods have been developed to improve the homogeneity of antibody-drug conjugates. In this regard, several site-specific labeling technologies have been developed and applied to prepare ADCs for pre-clinical and clinical studies. For example, improved antibody-drug conjugates, THIOMAB™, have been developed that provide for site-specific conjugation of a drug to an antibody through cysteine substitutions at sites where the engineered cysteines are available for conjugation but do not perturb immunoglobulin folding and assembly or alter antigen binding and effector functions (Junutula, et al, 2008b Nature Biotech., 26(8):925-932; Doman et al. (2009) Blood 114(13):2721-2729; U.S. Pat. Nos. 7,521,541; 7,723, 485; WO2009/052249). These THIOMAB™ antibodies can then be conjugated to cytotoxic drugs through the engineered cysteine thiol groups to obtain THIOMAB™ drug conjugates (TDC) with uniform stoichiometry (e.g., up to 2 drugs per antibody in an antibody that has a single engineered cysteine site). Studies with multiple antibodies against different antigens have shown that TDCs are as efficacious as conventional antibody-drug conjugate in xenograft models and are tolerated at higher doses in relevant preclinical models. THIOMAB™ antibodies have been engineered for drug attachment at different locations of the antibody (e.g., specific amino acid positions (i.e., sites) within the light chain-Fab, heavy chain-Fab and heavy chain-Fc). The in vitro and in vivo stability, efficacy and PK properties of THIOMAB™ antibodies provide a unique advantage over conventional antibody-drug conjugates due to their homogeneity and site-specific conjugation to cytotoxic drugs. However, those technologies involve protein engineering and/or enzyme catalysis, so that those technologies suffer from several drawbacks, such as lower level of antibody expression, complicated purification, and high cost.

WO 2006/065533 recognizes that the therapeutic index of antibody-drug conjugates can be improved by reducing the drug loading stoichiometry of the antibody below 8 drug molecules/antibody, and discloses engineered antibodies with predetermined sites for stoichiometric drug attachment. The 8 cysteine residues of the parent antibody involved in the formation of interchain disulfide bonds were each systematically replaced with another amino acid residue, to generate antibody variants with either 6, 4 or 2 remaining accessible cysteine residues. Antibody variants with 4 remaining cysteine residues were then used to generate conjugates displaying defined stoichiometry (4 drugs/antibody) and sites of drug attachment, which displayed similar antigen-binding affinity and cytotoxic activity to the more heterogeneous "partially-loaded" 4 drugs/antibody conjugates derived from previous methods. While the antibodies of WO 2006/065533 generate homogeneous conjugates with improved yield, it is thought that the elimination of the native interchain disulfide bonds could disrupt the quaternary structure of the antibody, thereby perturbing the behavior of the antibody in vivo, including changes in antibody effector functions (Junutula J R, et al. Nat Biotechnol. 2008 August; 26(8):925-32).

WO 2008/141044 is directed to antibody variants in which one or more amino acids of the antibody is substituted with a cysteine amino acid. The engineered cysteine amino acid residue is a free amino acid and not part of an intrachain or interchain disulfide bond, allowing drugs to be conjugated with defined stoichiometry and without disruption of the native disulfide bonds. There remains, however, a risk that engineering free cysteine residues into the antibody molecule may cause rearrangement and scrambling reactions with existing cysteine residues in the molecule during antibody folding and assembly, or result in dimerization through reaction with a free cysteine residue in another antibody molecule, leading to impaired antibody function or aggregation.

Therefore, there is a continuing need for developing a novel bio-conjugation process which can generate ADCs with improved homogeneity, and has simple manipulation and reduced cost.

SUMMARY OF INVENTION

The present disclosure has an object to develop a novel bio-conjugation process which can generate ADCs with improved homogeneity, and has simple manipulation and reduced cost. The ADCs with improved homogeneity generated by the bio-conjugation process of the disclosure further have optimized safety and efficacy.

The present disclosure relates to a novel bio-conjugation process for preparing antibody-drug conjugates (ADC) with improved homogeneity. As compared with conventional conjugation process involving the use of reductants and nucleophilic reaction of thiol groups, the homogeneity of antibody-drug conjugate (ADC) products generated from the bio-conjugation process of the present disclosure can be dramatically improved.

The bio-conjugation process for preparing antibody-drug conjugates (ADCs) with improved homogeneity comprises the following steps:

(a) incubating a reductant (e.g., Tris(2-carboxyethyl) phosphine (TCEP)), and the antibody to be conjugated in the presence of an effective amount of transition metal ions (e.g., $Zn^{2+}$, etc.) in a buffer system (e.g., Hepes, Histidine buffer, PBS, MES, etc.) to selectively reduce inter-chain disulfide bonds within the antibody;

(b) introducing an excess amount of payload bearing reactive groups (e.g., maleimide linking drugs, etc.) to react with reduced thiol groups resulted from step (a); and (c) adding an effective amount of oxidant (e.g., dehydroascorbic acid (DHAA)) to re-oxidize unreacted thiol groups, and then recovering the resultant antibody-drug conjugates.

In the present disclosure, transition metal ions generate selectivity in disulfide reduction. In the presence of transition metal ions, the two interchain S—S bonds in Fab regions are selectively reduced. And thus, four payload bearing reactive groups (i.e., four drug-linker complexes) are attached to one antibody to form D4. A high content of D4 in the resultant ADCs certainly improve the homogeneity of the ADCs.

The reductant may be TCEP. The concentration of the reductant in the reaction solution may be 0.04 mM—0.4 mM. The oxidant to be added in step (c) may be DHAA. The concentration of the oxidant in the reaction solution may be 0.08 mM—0.8 mM.

The transition metal ion which is suitable to be used in the bio-conjugation process of the present disclosure may include, but not limited to, $Zn^{2+}$, $Cd^{2+}$, $Hg^{2+}$, and the like. Among others, $Zn^{2+}$ is used due to its easily availability and low cost. For example, suitable transition metal salts may be added in step (a) as long as they are soluble in the reaction solution so that free transition metal ions can be released in the reaction solution. In this regard, $ZnCl_2$, $Zn(NO_3)_2$, $ZnSO_4$, $Zn(CH_3COO)_2$, $ZnI_2$, $ZnBr_2$, Zinc Formate, and zinc tetrafluoroborate may be mentioned as suitable zinc salts. Likewise, other transition metal salts which are soluble and can release free $Cd^{2+}$, or $Hg^{2+}$ ions in the reaction solution can be mentioned, which include, but not limited to, $CdCl_2$, $Cd(NO_3)_2$, $CdSO_4$, $Cd(CH_3COO)_2$, $CdI_2$, $CdBr_2$, cadmium formate, and cadmium tetrafluoroborate; $HgCl_2$, $Hg(NO_3)_2$, $HgSO_4$, $Hg(CH_3COO)_2$, $HgBr_2$, Mercury(II) formate, and Mercury(II) tetrafluoroborate; and the like.

In one embodiment, the concentration of the transition metal ions in step (a) is 0.01 mM—0.2 mM.

The transition metal ions will be removed in purification step by using EDTA as chelating reagent, which will be filtered out in subsequent dialysis, ultrafiltration or gel filtration.

Depending on the transition metal ions, those skilled in the art can select suitable buffer system for the reaction in step (a), including, but not limited to, Hepes, Histidine buffer, PBS, MES, and the like.

The optimum pH for the reaction will typically between about 5.5 and about 8, for instance, about 5.5 to 7.5. The optimal reaction conditions will of course depend upon the specific reactants employed.

The incubation time and temperature can be determined by those skilled in the art based on the specific antibody to be conjugated. The optimum temperature for the reaction may typically between about −10 and 37° C. For example, the reaction may occur at a temperature between about 0 and 20° C. overnight.

There is no specific limitation to the antibody which can be conjugated with a linker-drug by using the bio-conjugation process of the present disclosure. The selection of the antibody depends on the diseases or disorder (e.g., a cancer) to be treated by the antibody-drug conjugates (ADCs). The antibody can specifically bind corresponding antigens expressed on cancer cells (also referred to as tumor-associated antigens (TAA)), viral antigens, or microbial antigens, have antibody-dependent cell-mediated phagocytosis (ADCP) activity, and have antitumor, antiviral or antimicrobial activity in vivo. The interchain S—S bonds in the antibody are the sites for attaching drug-linker complex.

In some embodiments, the antibody may include, but not limited to, a monoclonal antibody or a polyclonal antibody. Specific examples of the antibody include a human antibody, a humanized antibody or a chimeric antibody. In certain embodiments, the antibody is a monoclonal antibody, for instance, a human antibody or a humanized antibody. As isotype of the antibody of the present disclosure, for example, IgG (IgG1, IgG2, IgG3, or IgG4) can be exemplified. In a specific embodiment, the antibody is an IgG1 monoclonal antibody. In another specific embodiment, the antibody is an IgG4 monoclonal antibody. For instance, three antibodies exemplified in the examples, Herceptin® (trastuzumab), Rituxan®(rituximab), and Erbitux®(cetuximab), are representative IgG1 type antibodies. The results of the examples demonstrate that the bio-conjugation process of the present disclosure is at least applicable to IgG1 type antibodies. Furthermore, the bio-conjugation process of the present disclosure may also be applicable to IgG4 type antibodies.

As for the payload bearing reactive group to be conjugated to the selected antibody, it generally has a format of drug-linker. There are no specific limitations to the drug and linker which can be used in the bio-conjugation process of the present disclosure, as long as the drug molecule has a desired (e.g., cytotoxic, antitumor, or labelling, etc.) effect and at least one substituted group or a partial structure allowing connection to a linker structure, and the linker contains at least two reactive groups, one of which can covalently bond a drug molecule and the other of which can covalently couple to an antibody.

A wide variety of diagnostic, therapeutic and labelling agents that are known in the art have been conjugated to antibody molecules. For example, in a broadest sense, the drug to be conjugated may include a diagnostic agent, a drug molecule, for example a cytotoxic agent, a toxin, a radionuclide, a fluorescent agent (for example an amine derivatized fluorescent probe such as 5-dimethylaminonaphthalene-1-(N-(2-aminoethyl))sulfonamide-dansyl ethylenediamine, Oregon Green® 488 cadaverine (catalogue number 0-10465, Molecular Probes), dansyl cadaverine, N-(2-aminoethyl)-4-amino-3,6-disulfo-1,8-naphthalimide, dipotassium salt (lucifer yellow ethylenediamine), or rhodamine B ethylenediamine (catalogue number L-2424, Molecular Probes), or a thiol derivatized fluorescent probe for example BODIPY® FLL-cystine (catalogue number B-20340, Molecular Probes)).

Depending on the desired drug and selected linker, those skilled in the art can select suitable method for coupling them together. For example, some conventional coupling methods, such as amine coupling methods, may be used to form the desired drug-linker complex which still contains reactive groups for conjugating to the antibodies through covalent linkage. A drug-maleimide complex (i.e., maleimide linking drug) is taken as an example of the payload bearing reactive group in the present disclosure. The drug may include, but not limited to, cytotoxic reagents, such as chemo-therapeutic agents, immunotherapeutic agents and the like, antiviral agents or antimicrobial agents. Most common reactive group capable of bonding to thiol group in ADC preparation is maleimide. Additionally, organic bromides, iodides also are frequently used.

As for step (c), those skilled in the art can select proper purification methods to recover the resultant antibody-drug conjugates. Many ADC purification methods are well known in the art. For example, the resultant antibody-drug conjugates may be purified by using a de-salting column, size exclusion chromatography, and the like.

With a conjugation process using the same steps without the addition of transition metal ions in step (a) as a negative control (see U.S. Pat. No. 7,659,241B2), the inventors successfully demonstrated that transition metal ions were the key factor responsible for higher level of D4 and lower level of D0, D6 and D8 in the resultant ADCs. Furthermore, the inventors also confirmed this new process generates ADC products with a high Fab preference. This process has been verified with several commercial therapeutic antibodies and showed great consistency.

By using the process of the present disclosure to produce antibody-drug conjugates, the homogeneity of the antibody-drug conjugates is higher than those produced by conventional conjugation processes. Specifically, in the ADCs prepared by the process of the present disclosure, the content of D0+D8 is less than 10 wt % and the content of D6 is less than 10 wt %. Moreover, the content of D4 is generally more than 65 wt %, and, for example, more than 70 wt %, while the content D4 is normally less than 40 wt % in the ADCs prepared by conventional conjugation processes.

The process of the present disclosure bypasses any need of protein engineering or enzyme catalysis, but is based on native inter-chain disulfide bonds and only needs transition metal ions. Therefore, as compared with conventional processes for preparing ADC, the process of the disclosure is less complicate, the homogeneity of the resultant antibody-drug conjugate is dramatically improved, and the cost will be highly reduced.

The foregoing and other features and advantages of the disclosure will become more apparent from the following detailed description of several embodiments which proceeds with reference to the accompanying figures.

DETAILED DESCRIPTION OF INVENTION

Figure 1:
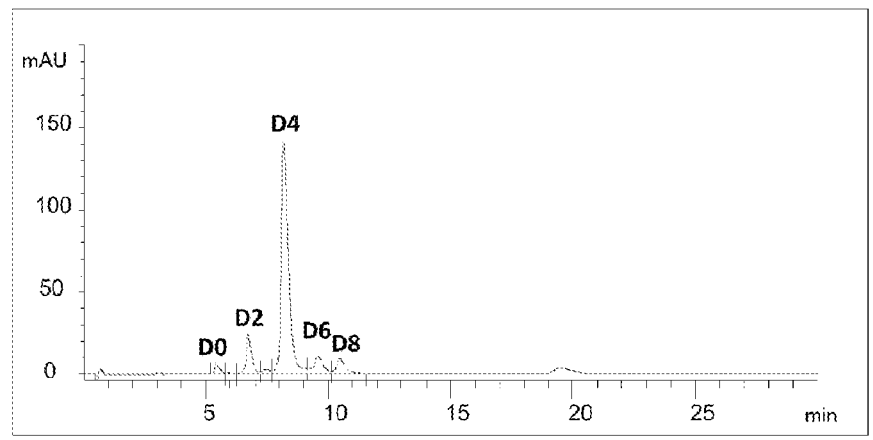
FIG. 1. HIC of Herceptin®(trastuzumab) MMAE conjugate prepared by using the process of the disclosure.

While the present disclosure may be embodied in many different forms, disclosed herein are specific illustrative embodiments thereof that exemplify the principles of the disclosure. It should be emphasized that the present disclosure is not limited to the specific embodiments illustrated. Moreover, any section headings used herein are for organizational purposes only and are not to be construed as limiting the subject matter described.

Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated. See, e.g., Abbas et al., Cellular and Molecular Immunology, 6th ed., W.B. Saunders Company (2010); Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual, Cold Spring Harbor Laboratory Press, Cold Spring Harbor, N.Y. (1998); and Coligan et al., Short Protocols in Protein Science, Wiley, John & Sons, Inc. (2003). The nomenclature used in connection with, and the laboratory procedures and techniques of, analytical chemistry, synthetic organic chemistry, and medicinal and pharmaceutical chemistry described herein are those well-known and commonly used in the art. Moreover, any section headings used herein are for organizational purposes only and are not to be construed as limiting the subject matter described.

DEFINITIONS

In order to better understand the disclosure, the definitions and explanations of the relevant terms are provided as follows.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "an antibody" includes a plurality of antibodies; reference to "a transition metal ion" includes mixtures of transition metal ions, and the like. In this application, the use of "or" means "and/or" unless stated otherwise.

Throughout this disclosure, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Reference throughout this disclosure to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

"Antibody-drug conjugate" or ADC refers to a conjugate formed by covalently coupling a drug to an antibody directly or indirectly via one or more suitable linkers. ADC is generally in a format of antibody-linker-drug conjugate. The Antibody-drug conjugates combine ideal properties of both antibodies and cytotoxic drugs by targeting potent cytotoxic drugs to the antigen-expressing tumor cells, thereby enhancing their anti-tumor activity.

The term"drug" as used herein refers to any cytotoxic molecule which has an antitumor effect and at least one substituted group or a partial structure allowing connection to a linker structure. The drug may kill cancer cells and/or inhibit growth, proliferation, or metastasis of cancer cells, thereby reducing, alleviating, or eliminating one or more symptoms of a disease or disorder.

The term "linker" as used herein refers to a reactive molecule which contains at least two reactive groups, one of which can covalently bond a drug molecule and the other of which can covalently couple to an antibody.

The term "antibody" as used herein encompasses any immunoglobulin, monoclonal antibody, polyclonal antibody, multispecific antibody, or bispecific (bivalent) antibody that binds to a specific antigen. A native intact antibody comprises two heavy chains and two light chains. Each heavy chain consists of a variable region ("HCVR") and a first, second, and third constant region (CH1, CH2 and CH3), while each light chain consists of a variable region ("LCVR") and a constant region (CL). Mammalian heavy chains are classified as α, δ, ε, γ, and μ, and mammalian light chains are classified as λ or κ. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for antibodies may be defined or identified by the conventions of Kabat, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A.M., J. Mol. Biol., 196,901 (1987); Chothia, C. et al., Nature. December 21-28; 342(6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. Each HCVR and LCVR comprises four FRs, and the CDRs and FRs are arranged from amino terminus to carboxy terminus in the order: FR1, CDR1, FR2, CDR2, FR3, CDR3, FR4. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

"Antibody fragments" comprise a portion of a full-length antibody, generally the antigen binding or variable region thereof. Examples of antibody fragments include Fab, Fab', F(ab')2, and Fv fragments; diabodies; linear antibodies; minibodies (Olafsen et al. (2004) Protein Eng. Design & Sel. 17(4):315-323), fragments produced by a Fab expression library, anti-idiotypic (anti-Id) antibodies, CDR (complementary determining region), and epitope-binding fragments of any described herein which immunospecifically bind to cancer cell antigens, viral antigens or microbial antigens, single-chain antibody molecules; and multispecific antibodies formed from antibody fragments.

The term "variable domain" with respect to an antibody as used herein refers to an antibody variable region or a fragment thereof comprising one or more CDRs. Although a variable domain may comprise an intact variable region (such as HCVR or LCVR), it is also possible to comprise less than an intact variable region yet still retain the capability of binding to an antigen or forming an antigen-binding site.

The term "antigen-binding moiety" as used herein refers to an antibody fragment formed from a portion of an antibody comprising one or more CDRs, or any other antibody fragment that binds to an antigen but does not comprise an intact native antibody structure. Examples of antigen-binding moiety include, without limitation, a variable domain, a variable region, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a multispecific antibody, a camelized single domain antibody, a nanobody, a domain antibody, and a bivalent domain antibody. An antigen-binding moiety is capable of binding to the same antigen to which the parent antibody binds. In certain embodiments, an antigen-binding moiety may comprise one or more CDRs from a particular human antibody grafted to a framework region from one or more different human antibodies. For more and detailed formats of antigen-binding moiety are described in Spiess et al, 2015 (Supra), and Brinkman et al., mAbs, 9(2), pp. 182-212 (2017), which are incorporated herein by their entirety.

"Fab" with regard to an antibody refers to that portion of the antibody consisting of a single light chain (both variable and constant regions) associating to the variable region and first constant region of a single heavy chain by a disulfide bond. In certain embodiments, the constant regions of both the light chain and heavy chain are replaced with TCR constant regions.

"Fab'" refers to a Fab fragment that includes a portion of the hinge region.

"F(ab')2" refers to a dimer of Fab'.

A "fragment difficult (Fd)" with regard to an antibody refers to the amino-terminal half of the heavy chain fragment that can be combined with the light chain to form Fab.

"Fc" with regard to an antibody refers to that portion of the antibody consisting of the second (CH2) and third (CH3) constant regions of a first heavy chain bound to the second and third constant regions of a second heavy chain via disulfide bonding. The Fc portion of the antibody is responsible for various effector functions such as ADCC, and CDC, but does not function in antigen binding.

"Hinge region" in terms of an antibody includes the portion of a heavy chain molecule that joins the CH1 domain to the CH2 domain. This hinge region comprises approximately 25 amino acid residues and is flexible, thus allowing the two N-terminus antigen binding regions to move independently.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see for example: U.S. Pat. Nos. 4,816,567; 5,807,715). The monoclonal antibodies may also be isolated from phage antibody libraries using the techniques described in Clackson et al. (1991) Nature, 352:624-628; Marks et al. (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

An "intact antibody" herein is one comprising a VL and VH domains, as well as a light chain constant domain (CL) and heavy chain constant domains, CH1, $CH_2$ and $CH_3$. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR Depending on the amino acid sequence of the constant domain of their heavy chains, intact antibodies can be assigned to different "classes". There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known. Ig forms include hinge-modifications or hingeless forms (Roux et al. (1998) J. Immunol. 161:4083-4090; Lund et al. (2000) Eur. J. Biochem. 267: 7246-7256; US 2005/0048572; US 2004/0229310).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all or at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al, J. Chromatogr. B 848:79-87 (2007).

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains ($CH_1$, $CH_2$, and $CH_3$). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

A "cysteine engineered antibody" or "cysteine engineered antibody variant" is an antibody in which one or more residues of an antibody are substituted with cysteine residues. In accordance with the present disclosure, the thiol group(s) of the cysteine engineered antibodies can be conjugated to calicheamicin to form a THIOMAB™ antibody (i.e., a THIOMAB™ drug conjugate (TDC), wherein in accordance with the present disclosure the drug is a calicheamicin derivative). In particular embodiments, the substituted residues occur at accessible sites of the antibody. By substituting those residues with cysteine, reactive thiol groups are thereby positioned at accessible sites of the antibody and may be used to conjugate the antibody to the drug moiety to create an immunoconjugate, as described further herein. For example, a THIOMAB™ antibody may be an antibody with a single mutation of a non-cysteine native residue to a cysteine in the light chain (e.g., G64C, K149C or R142C according to Kabat numbering) or in the heavy chain (e.g., D101C or V184C or T205C according to Kabat numbering). In specific examples, a THIOMAB™ antibody has a single cysteine mutation in either the heavy or light chain such that each full-length antibody (i.e., an antibody with two heavy chains and two light chains) has two engineered cysteine residues. Cysteine engineered antibodies and preparatory methods are disclosed by US 2012/0121615 A1 (incorporated by reference herein in its entirety).

A "disulfide bond" refers to a covalent bond with the structure R—S—S—R'. The amino acid cysteine comprises a thiol group that can form a disulfide bond with a second thiol group, for example from another cysteine residue. The disulfide bond can be formed between the thiol groups of two cysteine residues residing respectively on the two polypeptide chains, thereby forming an interchain bridge or interchain bond.

The term "specific binding" or "specifically binds" as used herein refers to a non-random binding reaction between two molecules, such as for example between an antibody and an antigen. In certain embodiments, the polypeptide complex and the bispecific polypeptide complex provided herein specifically bind an antigen with a binding affinity ($K_D$) of $\leq 10^{-6}$ M (e.g., $\leq 5 \times 10^{-7}$ M, $\leq 2 \times 10^{-7}$ M, $\leq 10^{-7}$ M, $\leq 5 \times 10^{-8}$ M, $\leq 2 \times 10^{-8}$ M, $\leq 10^{-8}$ M, $\leq 5 \times 10^{-9}$ M, $\leq 2 \times 10^{-9}$ M, $\leq 10^{-9}$ M, or $\leq 10^{-10}$ M). $K_D$ as used herein refers to the ratio of the dissociation rate to the association rate (koff/kon), may be determined using surface plasmon resonance methods for example using instrument such as Biacore.

The term "transition metal", as used herein, refers to the elements of groups 4-11, justified by their typical chemistry, i.e. a large range of complex ions in various oxidation states, colored complexes, and catalytic properties either as the element or as ions (or both). Sc and Y in Group 3 are also generally recognized as transition metals.

As discussed above, a mixture of antibody-drug conjugates will be generated by the conventional conjugation processes or the bio-conjugation process of the present disclosure. In general, one antibody molecule belonging to IgG1 or IgG4 subclass has 4 inter-chain S—S bonds, each of which is formed with two —SH groups. The antibody molecule can be subjected to partial or complete reduction of one or more interchain S—S bonds to form 2n (n is an integer selected from 1, 2, 3 or 4) reactive —SH groups, and thus, the number of drugs coupling to a single antibody molecule is 2, 4, 6 or 8. In accordance with the number of drugs coupling to a single antibody molecule, the different conjugates containing different number of drug molecules are denominated as D0, D2, D4, D6 and D8. If the number of drugs coupling to a single antibody molecule is 0, the product is referred to as D0. Accordingly, D2 refers to the ADC in which two drug molecules are coupled to one single antibody molecule, where two drug molecules may be coupled to —SH groups generated by reduction of S—S bonds between heavy and light chains via linkers, or may be coupled to —SH groups generated by reduction of S—S bonds between heavy and heavy chains via linkers. D4 refers to the ADC in which four drug molecules are coupled to one single antibody molecule, where four drug molecules may be coupled to four —SH groups generated by reduction of two S—S bonds between heavy and light chains via linkers (such ADC is referred to as D4-1), or four drug molecules may be coupled to four —SH groups generated by reduction of two S—S bonds between heavy and heavy chains via linkers (such ADC is referred to as D4-2), or two drug molecules may be coupled to two —SH groups generated by reduction of one S—S bond between heavy and light chains via linkers and the other two drug molecules may be coupled to two —SH groups generated by reduction of one S—S bond between heavy and heavy chains vis linkers (such ADC is referred to as D4-3). D6 refers to the ADC in which six drug molecules are coupled to one single antibody molecule, where four drug molecules may be coupled to four —SH groups generated by reduction of two S—S bonds between heavy and light chains via linkers and two drug molecules may be coupled to two —SH groups generated by reduction of one S—S bonds between heavy and heavy chains via linkers (such ADC is referred to as D6-1), or four drug molecules may be coupled to four —SH groups generated by reduction of two S—S bonds between heavy and heavy chains via linkers and two drug molecules may be coupled to two —SH groups generated by reduction of one S—S bonds between heavy and light chains via linkers (such ADC is referred to as D6-2). And D8 refers to the ADC in which eight drug molecules are coupled to one single antibody molecule, i.e., all the four S—S bonds in one antibody molecule are reduced to eight —SH groups and each —SH group attaches one drug molecule. In general, the heterogeneous mixture of ADC molecules generated by conventional conjugation processes or the bio-conjugation process of the present disclosure is a mixture of D0, D2, D4, D6 and D8. And thus, the "homogeneity" of antibody-drug conjugates is used to describe the property of dominance of one specific type of antibody-drug conjugate (i.e., one type selected from D0, D2, D4, D6 and D8 conjugates) in one given mixture of antibody-drug conjugates. Although antibody-drug conjugate potency in vitro has been shown to be directly dependent on drug loading (Hamblett K J, et al., Clin Cancer Res. 2004 Oct. 15; 10(20):7063-70), in-vivo therapeutic activity (e.g., antitumour) of antibody-drug conjugates with four drugs per molecule (D4) is comparable with conjugates with eight drugs per molecule (D8) at equal mAb doses, even though the conjugates contains half the amount of drug per mAb. Drug-loading also affects plasma clearance, with the D8 conjugate being cleared 3-fold faster than the D4 conjugate and 5-fold faster than a D2 conjugate. In general, if the content of D4 is high in the mixture, the ADCs are considered to have a high homogeneity. In the present disclosure, the "homogeneity" of antibody-drug conjugates refers to a high level of D4 in the mixture of antibody-drug conjugates.

Accordingly, "improved homogeneity" of ADCs, as used herein, refers to a higher level of D4 in the mixture of antibody-drug conjugates generated by the process of the present disclosure as compared with the mixture of ADCs generated by conventional conjugation processes. In the ADCs prepared by the process of the present disclosure, the content of D4 is generally more than 65 wt %, for example, more than 70 wt %, while the content of D4 is normally less than 40% in the ADCs prepared by conventional conjugation processes.

The term "antibody-dependent cell-mediated cytotoxicity" or "ADCC", as used herein, refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No.

5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The term "complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202: 163 (1996), may be performed.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

A "pharmaceutically acceptable carrier" refers to an ingredient in a pharmaceutical formulation, other than an active ingredient, which is bioactivity acceptable and nontoxic to a subject. Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispensing agents, sequestering or chelating agents, diluents, adjuvants, excipients, or nontoxic auxiliary substances, other components known in the art, or various combinations thereof.

The term "subject" includes any human or nonhuman animal, for example, humans.

The term "cancer", as used herein, refers to any or a tumor or a malignant cell growth, proliferation or metastasis-mediated, solid tumors and non-solid tumors such as leukemia and initiate a medical condition. A "tumor" comprises one or more cancerous cells. Examples of cancer include, but are not limited to, carcinoma, lymphoma, blastema, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "treatment", "treating" or "treated", as used herein in the context of treating a condition, pertains generally to treatment and therapy, whether of a human or an animal, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included. For cancer, "treating" may refer to dampen or slow the tumor or malignant cell growth, proliferation, or metastasis, or some combination thereof. For tumors, "treatment" includes removal of all or part of the tumor, inhibiting or slowing tumor growth and metastasis, preventing or delaying the development of a tumor, or some combination thereof.

The antibody is against tumor-associated antigens (TAA), an antigen of a cell that is responsible for producing autoimmune antibodies, a viral or a microbial antigen. Tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of tumor-associated antigens TAA include, but are not limited to, TAA (1)-(53) listed herein. For convenience, information relating to these antigens, all of which are known in the art, is listed herein and includes names, alternative names, Genbank accession numbers and primary reference(s), following nucleic acid and protein sequence identification conventions of the National Center for Biotechnology Information (NCBI) (see WO2017068511A1, which is entirely incorporated herein by reference). Nucleic acid and protein sequences corresponding to TAA (1)-(53) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens (TAA)

Figure 4:
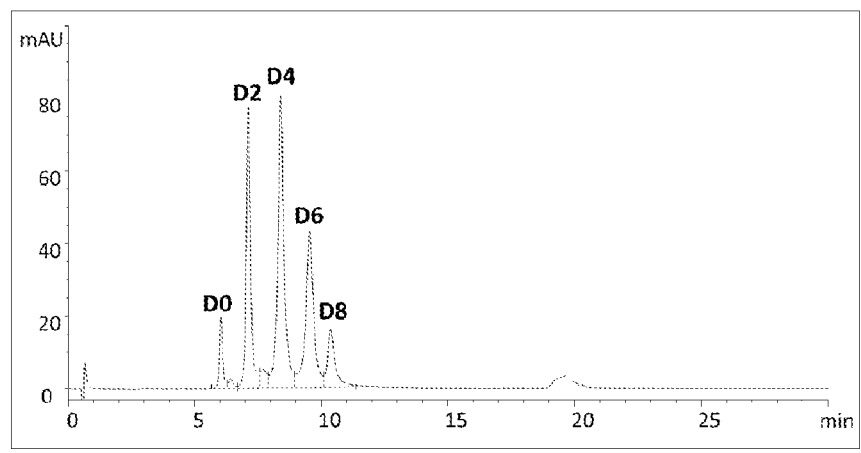
FIG. 4. HIC of Erbitux®(cetuximab) MMAE conjugate prepared by using conventional method.

(1) BMPRIB (bone morphogenetic protein receptor-type 1B, Genbank accession no. NM_001203) ten Dijke, P., et al. Science 264 (5155): 101-104 (1994), Oncogene 14 (11): 1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377 (Page 349-350); WO200230268 (Claim 27; Page 376); WO200148204 (Example; FIG. 4) NP_001194 bone morphogenetic protein receptor, type IB/pid=NP_001194.1—Cross-references: MIM:603248; NP_001194.1; AY065994.

Figure 3:
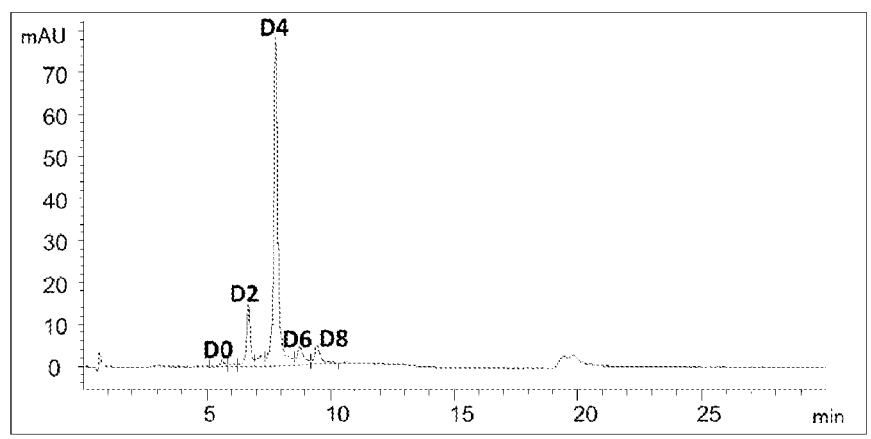
FIG. 3. HIC of Erbitux®(cetuximab) MMAE conjugate prepared by using the process of the disclosure.

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al. (1992) J. Biol. Chem. 267 (16): 11267-11273); WO2004048938 (Example 2); WO2004032842 (Example IV); WO2003042661 (Claim 12);

WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150); NP_003477 solute carrier family 7 (cationic amino acid transporter, y+ system), member 5/pid=NP_003477.3—*Homo sapiens* Cross-references: MIM:600182; NP_003477.3; NM_015923; NM_003486_1.

Figure 2:
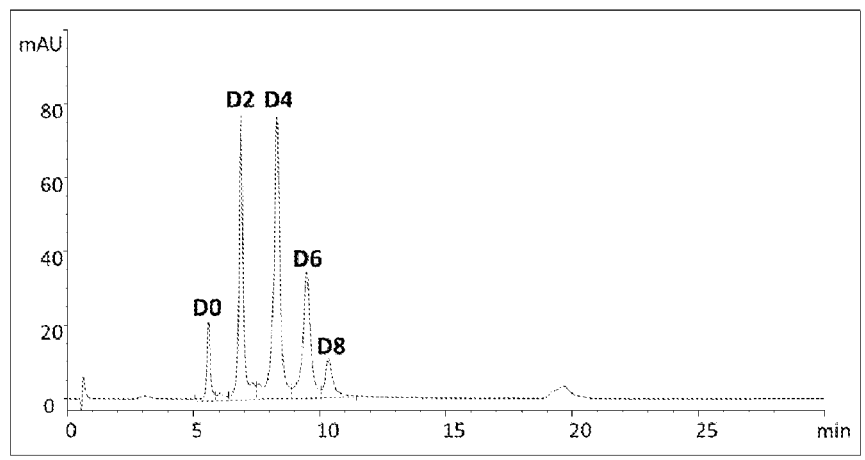
FIG. 2. HIC of Herceptin®(trastuzumab) MMAE conjugate prepared by using conventional method.

(3) STEAP1 (six transmembrane epithelial antigen of prostate, Genbank accession no. NM_012449) Cancer Res. 61 (15), 5857-5860 (2001), Hubert, R. S., et al. (1999) Proc. Natl. Acad. Sci. U.S.A. 96 (25): 14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate Cross-references: MIM:604415; NP_036581.1; NM_012449_1.

(4) 0772P (CA125, MUC16, Genbank accession no. AF361486) J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); U.S. Pat. No. 798,959. Cross-references: GI:34501467; AAK74120.3; AF361486_1.

(5) MPF (MPF, MSLN, SMR, megakaryocyte potentiating factor, mesothelin, Genbank accession no. NM_005823), Yamaguchi, N., et al. Biol. Chem. 269 (2), 805-808 (1994), Proc. Natl. Acad. Sci. U.S.A. 96 (20): 11531-11536 (1999), Proc. Natl. Acad. Sci. U.S.A. 93 (1): 136-140 (1996), J. Biol. Chem. 270 (37):21984-21990 (1995)); WO2003101283 (Claim 14); WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1.

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22): 19665-19672 (2002), Genomics 62 (2):281-284 (1999), J. A., et al. (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140); Cross-references: MIM:604217; NP_006415.1; NM_006424_1.

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin)5B, Genbank accession no. AB040878) Nagase T., et al. (2000) DNA Res. 7 (2): 143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC: 10737.

(8) PSCA hlg (2700050C12Rik, C530008016Rik, RIKEN cDNA 2700050C12, RIKEN cDNA 2700050C12 gene, Genbank accession no. AY358628); Ross et al. (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20); Cross-references: GE37182378; AAQ88991.1; AY358628_1.

Figure 6:
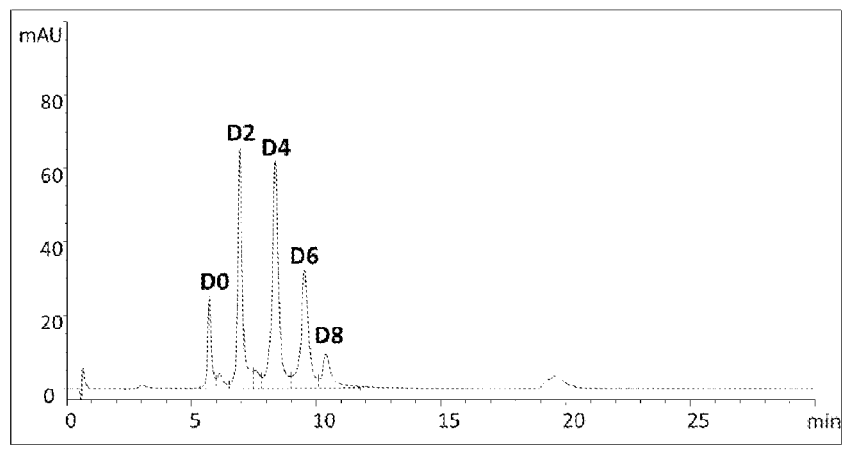
FIG. 6. HIC of Rituxan®(rituximab) MMAE conjugate prepared by using conventional method.

(9) ETBR (Endothelin type B receptor, Genbank accession no. AY275463); Nakamuta M., et al. Biochem. Biophys. Res. Commun. 177,34-39, 1991; Ogawa Y., et al. Biochem. Biophys. Res. Commun. 178, 248-255, 1991; Arai H., et al. Jpn. Circ. J. 56, 1303-1307, 1992; Arai H., et al. J. Biol. Chem. 268, 3463-3470, 1993; Sakamoto A., Yanagisawa M., et al. Biochem. Biophys. Res. Commun. 178, 656-663, 1991; Elshourbagy N. A., et al. J. Biol. Chem. 268,3873-3879, 1993; Haendler B., et al. J. Cardiovasc. Pharmacol. 20, s1-S4, 1992; Tsutsumi M., et al. Gene 228, 43-49, 1999; Strausberg R. L., et al. Proc. Natl. Acad. Sci. U.S.A. 99, 16899-16903, 2002; Bourgeois C, et al. J. Clin. Endocrinol. Metab. 82, 3116-3123, 1997; Okamoto Y., et al. Biol. Chem. 272, 21589-21596, 1997; Verheij J. B., et al. Am. J. Med. Genet. 108, 223-225, 2002; Hofstra R M. W., et al. Eur. J. Hum. Genet. 5, 180-185, 1997; Puffenberger E. G., et al. Cell 79, 1257-1266, 1994; Attie T., et al., Hum. Mol. Genet. 4, 2407-2409, 1995; Auricchio A., et al. Hum. Mol. Genet 5:351-354, 1996; Amiel J., et al. Hum. Mol. Genet. 5, 355-357, 1996; Hofstra R M. W., et al. Nat. Genet. 12, 445-447, 1996; Svensson P. J., et al. Hum. Genet. 103, 145-148, 1998; Fuchs S., et al. Mol. Med. 7, 115-124, 2001; Pingault V., et al. (2002) Hum. Genet. Ill, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004.

(10) MSG783 (RNF124, hypothetical protein FLJ20315, Genbank accession no. NM_017763); WO2003104275 (Claim 1); WO2004046342(Example 2); WO2003042661 (Claim 12); WO2003083074 (Claim 14; Page 61); WO2003018621 (Claim 1); WO2003024392 (Claim 2; FIG. 93); WO200166689 (Example 6); Cross-references: Locus ID: 54894; NP_060233.2; NM_017763_1.

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138); Lab. Invest. 82 (11): 1573-1582 (2002); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10); Cross-references: GE22655488; AAN04080.1; AF455138_1.

(12) TrpM4 (BR22450, FLJ20041, TRPM4, TRPM4B, transient receptor potential cation channel, subfamily M, member 4, Genbank accession no. NM_017636) Xu, X. Z., et al. Proc. Natl. Acad. Sci. U.S.A. 98 (19): 10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12);

WO200230268 (Claim 27; Page 391); US2003219806 (Claim 4); WO200162794 (Claim 14; FIG. 1A-D); Cross-references: MIM:606936; NP_060106.2; NM_017636_1.

(13) CRIPTO (CR, CR1, CRGF, CRIPTO, TDGF1, teratocarcinoma-derived growth factor, Genbank accession no. NP_003203 or NM_003212) Ciccodicola, A., et al. EMBO J. 8 (7): 1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2); Cross-references: MIM: 187395; NP_003203.1; NM_003212_1.

(14) CD21 (CR2 (Complement receptor 2) or C3DR (C3d/Epstein Barr virus receptor) or Hs.73792 Genbank accession no. M26004) Fujisaku et al. (1989) J. Biol. Chem. 264 (4):2118-2125; Weis J. J., et al. J. Exp. Med. 167, 1047-1066, 1988; Moore M., et al. Proc. Natl. Acad. Sci. U.S.A. 84,9194-9198, 1987; Barel M., et al. Mol. Immunol. 35, 1025-1031, 1998; Weis J. J., et al. Proc. Natl. Acad. Sci. U.S.A. 83, 5639-5643, 1986; Sinha S. K., et al. (1993) J. Immunol. 150, 5311-5320; WO2004045520 (Example 4); US2004005538 (Example 1); WO2003062401 (Claim 9); WO2004045520 (Example 4); WO9102536 (FIGS. 9.1-9.9); WO2004020595 (Claim 1); Accession: P20023; Q13866; Q14212; EMBL; M26004; AAA35786.1.

(15) CD79b (CD79B, CD79O, IGb (immunoglobulin-associated beta), B29, Genbank accession no. NM_000626 or 11038674) Proc. Natl. Acad. Sci. U.S.A. (2003) 100 (7):4126-4131, Blood (2002) 100 (9):3068-3076, Muller et al. (1992) Eur. J. Immunol. 22 (6): 1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146); Cross-references: MIM: 147245; NP_000617.1; NM_000626_1.

(16) FcRH2 (IFGP4, IRTA4, SPAP1A (SH2 domain containing phosphatase anchor protein 1a), SPAP1B, SPAP1C, Genbank accession no. NM_030764, AY358130) Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al. (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25); Cross-references: MIM:606509; NP_110391.2; NM_030764_1.

(17) HER2(ErbB2, Genbank accession no. M 11730) Coussens L., et al. Science (1985) 230(4730): 1132-1139); Yamamoto T., et al. Nature 319, 230-234, 1986; Semba K., et al. Proc. Natl. Acad. Sci. U.S.A. 82, 6497-6501, 1985; Swiercz J. M., et al. J. Cell Biol. 165, 869-880, 2004; Kuhns J. J., et al. J. Biol. Chem. 274, 36422-36427, 1999; Cho H.-S., et al. Nature 421, 756-760, 2003; Ehsani A., et al. (1993) Genomics 15, 426-429; WO2004048938 (Example 2); WO2004027049 (FIG. II); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP 1439393 (Claim 7); WO2004043361 (Claim 7); WO2004022709; WO200100244 (Example 3; FIG. 4); Accession: P04626; EMBL; M11767; AAA35808.1. EMBL; M11761; AAA35808.1.

(18) NCA (CEACAM6, Genbank accession no. M18728); Barnett T., et al. Genomics 3, 59-66, 1988; Tawaragi Y., et al. Biochem. Biophys. Res. Commun. 150, 89-96, 1988; Strausberg R. L., et al. Proc. Natl. Acad. Sci. U.S.A. 99: 16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2); Accession: P40199; Q14920; EMBL; M29541; AAA59915.1. EMBL; M18728.

(19) MDP (DPEP1, Genbank accession no. BC017023) Proc. Natl. Acad. Sci. U.S.A. 99 (26): 16899-16903 (2002)); WO2003016475 (Claim 1); WO200264798 (Claim 33; Page 85-87); JP05003790 (FIG. 6-8); WO9946284 (FIG. 9); Cross-references: MIM: 179780; AAH17023.1; BC017023_1.

(20) IL20Rα (IL20Rα, ZCYTOR7, Genbank accession no. AF184971); Clark H. F., et al. Genome Res. 13, 2265-2270, 2003; Mungall A. J., et al. Nature 425, 805-811, 2003; Blumberg H., et al. Cell 104, 9-19, 2001; Dumoutier L., et al. J. Immunol. 167, 3545-3549, 2001; Parrish-Novak J., et al. J. Biol. Chem. 277, 47517-47523, 2002; Pletnev S., et al. (2003) Biochemistry 42: 12617-12624; Sheikh F., et al. (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF184971; AAF01320.1.

(21) Brevican (BCAN, BEHAB, Genbank accession no. AF229053) Gary S. C., et al. Gene 256, 139-147, 2000; Clark H. F., et al. Genome Res. 13, 2265-2270, 2003; Strausberg R. L., et al. Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1).

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196: 177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); Cross-references: MIM: 600997; NP_004433.2; NM_004442_1.

(23) ASLG659 (B7h, Genbank accession no. AX092328) US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46);

WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318.

(24) PSCA (Prostate stem cell antigen precursor, Genbank accession no. AJ297436) Reiter R. E., et al. Proc. Natl. Acad. Sci. U.S.A. 95, 1735-1740, 1998; Gu Z., et al. Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B); Accession: O43653; EMBL; AF043498; AAC39607.1.

(25) GEDA (Genbank accession No. AY260763); AAP14954 lipoma HMGIC fusion-partner-like protein/pid=AAP14954.1—*Homo sapiens* Species: *Homo sapiens* (human) WO2003054152 (Claim 20); WO2003000842 (Claim 1); WO2003023013 (Example 3, Claim 20); US2003194704 (Claim 45); Cross-references: GI:30102449; AAP14954.1; AY260763_1.

(26) BAFF-R (B cell-activating factor receptor, BLyS receptor 3, BR3, Genbank accession No. AF116456); BAFF receptor/pid=NP_443177.1—*Homo sapiens* Thompson, J. S., et al. Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3); Cross-references: MIM: 606269; NP 443177.1; NM_052945_1; AF132600.

(27) CD22 (B-cell receptor CD22-B isoform, BL-CAM, Lyb-8, Lyb8, SIGLEC-2, FLJ22814, Genbank accession No. AK026467); Wilson et al. (1991) J. Exp. Med. 173: 137-146; WO2003072036 (Claim 1; FIG. 1); Cross-references: MIM: 107266; NP_001762.1; NM_001771_1.

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation, pI: 4.84, MW: 25028 TM: 2 [P] Gene Chromosome: 19ql3.2, Genbank accession No. NP_001774.10) WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al. (1992) J. Immunol. 148(5): 1526-1531; Mueller et al. (1992) Eur. J. Biochem. 22: 1621-1625; Hashimoto et al. (1994) Immunogenetics 40(4):287-295; Preud'homme et al. (1992) Clin. Exp. Immunol. 90(1): 141-146; Yu et al. (1992) J. Immunol. 148(2) 633-637; Sakaguchi et al. (1988) EMBO J. 7(11): 3457-3464.

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1) WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al. (1992) Eur. J. Immunol. 22:2795-2799; Barella et al. (1995) Biochem. J. 309:773-779.

(30) HLA-DOB (Beta subunit of MHC class II molecule (Ia antigen) that binds peptides and presents them to CD4+ T lymphocytes); 273 aa, pI: 6.56 MW: 30820 TM: 1 [P] Gene Chromosome: 6p21.3, Genbank accession No. NP_002111.1) Tonnelle et al. (1985) EMBO J. 4(11):2839-2847; Jonsson et al. (1989) Immunogenetics 29(6):411-413; Beck et al. (1992) J. Mol. Biol. 228:433-441; Strausberg et al. (2002) Proc. Natl. Acad. Sci USA 99: 16899-16903; Servenius et al. (1987) J. Biol. Chem. 262:8759-8766; Beck et al. (1996) J. Mol. Biol. 255: 1-13; Naruse et al. (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al. (1989) Immunogenetics 30(1):66-68; Larhammar et al. (1985) J. Biol. Chem. 260(26): 14111-14119.

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa, pI: 7.63, MW: 47206 TM: 1 [P] Gene Chromosome: 17p13.3, Genbank accession No. NP_002552.2) Le et al. (1997) FEBS Lett. 418(1-2): 195-199; WO2004047749; WO2003072035 (claim 10); Touchman et al. (2000) Genome Res. 10: 165-173; WO200222660 (claim 20); WO2003093444 (claim 1); WO2003087768 (claim 1); WO2003029277 (page 82).

(32) CD72 (B-cell differentiation antigen CD72, Lyb-2, PROTEIN SEQUENCE Full maeaity . . . tafrfpd (1.359; 359 aa), pI: 8.66, MW: 40225 TM: 1 [P] Gene Chromosome: 9p13.3, Genbank accession No. NP_001773.1) WO2004042346 (claim 65); WO2003026493 (pages 51-52, 57-58); WO200075655 (pages 105-106); Von Hoegen et al. (1990) J. Immunol. 144(12):4870-4877; Strausberg et al. (2002) Proc. Natl. Acad. Sci USA 99: 16899-16903.

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1) US2002193567; WO9707198 (claim 11, pages 39-42); Miura et al. (1996) Genomics 38(3):299-304; Miura et al. (1998) Blood 92:2815-2822; WO2003083047; WO9744452 (claim 8, pages 57-61); WO200012130 (pages 24-26).

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1) WO2003077836; WO200138490 (claim 6, FIG. 18E-1-18-E-2); Davis et al. (2001) Proc. Natl. Acad. Sci USA 98(17):9772-9777; WO2003089624 (claim 8); EP1347046 (claim 1); WO2003089624 (claim 7).

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P]

Gene Chromosome: 1q21, Genbank accession No. Human: AF343662, AF343663, AF343664, AF343665, AF369794, AF397453, AK090423, AK090475, AL834187, AY358085; Mouse:AK089756, AY158090, AY506558; NP_112571.1. WO2003024392 (claim 2, FIG. 97); Nakayama et al. (2000) Biochem. Biophys. Res. Commun. 277(1): 124-127; WO2003077836; WO200138490 (claim 3, FIG. 18B-1 to 18B-2).

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436 WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al. (2000) Genomics 67: 146-152; Uchida et al. (1999) Biochem. Biophys. Res. Commun. 266:593-602; Liang et al. (2000) Cancer Res. 60:4907-12; Glynne-Jones et al. (2001) Int J Cancer. October 15; 94(2): 178-84.

(37) PMEL17 (silver homolog; SILV; D12S53E; PMEL17; SI; SIL); ME20; gp100) BC001414; BT007202; M32295; M77348; NM_006928; McGlinchey, R. P. et al. (2009) Proc. Natl. Acad. Sci. U.S.A. 106 (33), 13731-13736; Kummer, M. P. et al. (2009) J. Biol. Chem. 284 (4), 2296-2306.

(38) TMEFF1 (transmembrane protein with EGF-like and two follistatin-like domains 1; Tomoregulin-1); H7365; C9orf2; C90RF2; U19878; X83961; NM_080655; NM_003692; Harms, P. W. (2003) Genes Dev. 17 (21), 2624-2629; Gery, S. et al. (2003) Oncogene 22 (18):2723-2727.

(39) GDNF-Ra1 (GDNF family receptor alpha 1; GFRA1; GDNFR; GDNFRA; RETLi; TRNR1; RET1L; GDNFR-alpha1; GFR-ALPHA-1); U95847; BC014962; NM 145793 NM_005264; Kim, M. H. et al. (2009) Mol. Cell. Biol. 29 (8), 2264-2277; Treanor, J. J. et al. (1996) Nature 382 (6586):80-83.

(40) Ly6E (lymphocyte antigen 6 complex, locus E; Ly67, RIG-E, SCA-2, TSA-1); NP_002337.1; NM_002346.2; de Nooij-van Dalen, A G. et al. (2003) Int. J. Cancer 103 (6), 768-774; Zammit, D. J. et al. (2002) Mol. Cell. Biol. 22 (3):946-952.

(41) TMEM46 (shisa homolog 2 (*Xenopus laevis*); SHISA2); NP_001007539.1; NM_001007538.1; Furushima, K. et al. (2007) Dev. Biol. 306 (2), 480-492; Clark, H. F. et al. (2003) Genome Res. 13 (10):2265-2270.

(42) Ly6G6D (lymphocyte antigen 6 complex, locus G6D; Ly6-D, MEGT1); NP_067079.2; NM_021246.2; Mallya, M. et al. (2002) Genomics 80 (1): 113-123; Ribas, G. et al. (1999) J. Immunol. 163 (1):278-287.

(43) LGR5 (leucine-rich repeat-containing G protein-coupled receptor 5; GPR49, GPR67); NP_003658.1; NM_003667.2; Salanti, G. et al. (2009) Am. J. Epidemiol. 170 (5):537-545; Yamamoto, Y. et al. (2003) Hepatology 37 (3):528-533.

(44) RET (ret proto-oncogene; MEN2A; HSCR1; MEN2B; MTC1; PTC; CDHF12; Hs.168114; RET51; RET-ELE1); NP_066124.1; NM_020975.4; Tsukamoto, H. et al. (2009) Cancer Sci. 100 (10): 1895-1901; Narita, N. et al. (2009) Oncogene 28 (34):3058-3068.

(45) LY6K (lymphocyte antigen 6 complex, locus K; LY6K; HSJ001348; FLJ35226); NP_059997.3; NM_017527.3; Ishikawa, N. et al. (2007) Cancer Res. 67 (24): 11601-11611; de Nooij-van Dalen, A G. et al. (2003) Int. J. Cancer 103 (6):768-774.

(46) GPR19 (G protein-coupled receptor 19; Mm.4787); NP_006134.1; NM_006143.2; Montpetit, A. and Sinnett, D. (1999) Hum. Genet. 105 (1-2): 162-164; O'Dowd, B. F. et al. (1996) FEBS Lett. 394 (3):325-329.

(47) GPR54 (KISS1 receptor; KISS1R; GPR54; HOT7T175; AXOR12); NP_115940.2; NM_032551.4; Navenot, J. M. et al. (2009) Mol. Pharmacol. 75 (6): 1300-1306; Hata, K. et al. (2009) Anticancer Res. 29 (2): 617-623.

(48) ASPHD1 (aspartate beta-hydroxylase domain containing 1; LOC253982); NP_859069.2; NM_181718.3; Gerhard, D. S. et al. (2004) Genome Res. 14 (10B):2121-2127.

(49) Tyrosinase (TYR; OCAIA; OCA1A; tyrosinase; SHEP3); NP_000363.1; NM_000372.4; Bishop, D. T. et al. (2009) Nat. Genet. 41 (8):920-925; Nan, H. et al. (2009) Int. J. Cancer 125 (4):909-917.

(50) TMEM118 (ring finger protein, transmembrane 2; RNFT2; FLJ14627); NP_001103373.1; NM_001109903.1; Clark, H. F. et al. (2003) Genome Res. 13 (10):2265-2270; Scherer, S. E. et al. (2006) Nature 440 (7082):346-351.

(51) GPR172A (G protein-coupled receptor 172A; GPCR41; FLJ11856; D15Ertd747e); NP_078807.1; NM_024531.3; Ericsson, T. A. et al. (2003) Proc. Natl. Acad. Sci. U.S.A. 100 (1 1):6759-6764; Takeda, S. et al. (2002) FEBS Lett 520 (1-3):97-101.

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) J. Clin. Invest. 75:756-56; Andrews et al., (1986) Blood 68: 1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al, (2007) Blood 110 (7):2659-66; Chen C H, et al. (2006) Blood 107 (4): 1459-67; Marshall A S, et al. (2006) Eur. J. Immunol. 36 (8):2159-69; Bakker A B, et al. (2005) Cancer Res. 64 (22): 8443-50; Marshall A S, et al. (2004) J. Biol. Chem. 279 (15): 14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

THE CONJUGATION PROCESS OF THE PRESENT INVENTION

In a first aspect, the present disclosure relates to a process for preparing antibody-drug conjugates (ADCs) with improved homogeneity comprising the following steps:
(a) incubating a reductant and the antibody to be conjugated in the presence of an effective amount of transition metal ions in a buffer system to selectively reduce inter-chain disulfide bonds within the antibody;
(b) introducing an excess amount of payload bearing reactive groups to react with reduced thiol groups resulted from step (a); and
(c) adding an effective amount of oxidant to re-oxidize the unreacted thiol groups, and then recovering the resultant antibody-drug conjugates.

Transition metal ions generate selectivity in disulfide reduction. In the presence of transition metal ions, the two interchain S—S bonds in Fab regions are selectively reduced. And thus, four payload bearing reactive groups (i.e., four drug-linker complexes) are attached to one antibody to form D4. A high content of D4 in the resultant ADCs certainly improve the homogeneity of the ADCs.

In some embodiments, the reductant may be TCEP. The concentration of the reductant in the reaction solution may be 0.04 mM to 0.4 mM. The oxidant to be added in step (c) may be DHAA. The concentration of the oxidant in the reaction solution may be 0.08 mM to 0.8 mM.

In some embodiments, the transition metal ion which is suitable to be used in the bio-conjugation process of the present disclosure may include, but not limited to, $Zn^{2+}$, $Cd^{2+}$, and $Hg^{2+}$, and the like. Among others, $Zn^{2+}$ is used due to its easily availability and low cost. For example, suitable transition metal salts may be added in step (a) as long as they are soluble in the reaction solution so that free transition metal ions can be released in the reaction solution. In this regard, $ZnCl_2$, $Zn(NO_3)_2$, $ZnSO_4$, $Zn(CH_3COO)_2$, $ZnI_2$, $ZnBr_2$, Zinc Formate, and zinc tetrafluoroborate may be mentioned as suitable zinc salts. Likewise, other transition metal salts which are soluble and can release free $Cd^{2+}$ or $Hg^{2+}$ ions in the reaction solution can be mentioned, which include, but not limited to, $CdCl_2$, $Cd(NO_3)_2$, $CdSO_4$, $Cd(CH_3COO)_2$, $CdI_2$, $CdBr_2$, cadmium formate, and cadmium tetrafluoroborate; $HgCl_2$, $Hg(NO_3)_2$, $HgSO_4$, $Hg(CH_3COO)_2$, $HgBr_2$, Mercury(II) formate, and Mercury (II) tetrafluoroborate; and the like. Those skilled in the art can make a selection from the above transition metal salts as the source of transition metal ions.

In an embodiment, $Zn^{2+}$ is used in step (a). Zinc salts which are water soluble are available. For example, $ZnCl_2$ may be added in step (a) as the $Zn^{2+}$ source.

The concentration of the transition metal ions in the reaction solution in step (a) is 0.01 mM to 0.2 mM.

The transition metal ions will be removed in purification step by using EDTA as chelating reagent, which will be filtered out in subsequent dialysis, ultrafiltration or gel filtration.

Depending on the transition metal ions, those skilled in the art can select suitable buffer system for the reaction in step (a), including, but not limited to, Hepes, Histidine buffer, PBS, MES, and the like. In a specific embodiment, the buffer system used in step (a) is PBS.

The optimum pH for the reaction will typically between about 5.5 and about 8, for instance, about 5.5 to 7.5. The optimal reaction conditions will of course depend upon the specific reactants employed.

In an embodiment, the buffer is PBS, pH 7.

The optimum temperature for the reaction will typically between about −10 and 37° C. The reaction occurs, for instance, at a temperature between about 0 and 20° C. overnight.

Those skilled in the art should understand that the incubation time period and temperature in step (a) depend on specific antibodies to be conjugated. The determination of the incubation time period and temperature based on specific antibodies is within the abilities of ordinary skilled persons in the art. For example, the antibody to be conjugated is typically incubated with the reductant in the presence of transitional metal ions at 4° C. overnight.

In some embodiments, the concentration of the antibody in the reaction is from 0.01 mM to 0.1 mM. In a specific embodiment, the concentration of the antibody is 0.02 mM.

For instance, the antibody to be conjugated, the transitional metal ions and the reductant may be present in the reaction mixture in a ratio of 1:2:4 in molar concentration. In one embodiment, 0.02 mM antibody is incubated with 0.08 mM TCEP and 0.04 mM $ZnCl_2$ at 4° C. overnight. It will be understood by a person skilled in the art that a molar concentration may also be converted into "eq," and 1 mM can be converted to 0.5 eq in the context of the present disclosure. For instance, "0.04 mM $ZnCl_2$" may be converted into "2 eq $ZnCl_2$".

There is no specific limitation to the antibody to be conjugated. According to the antigens associated with the disease or disorder (e.g., specific tumor-associated antigens, viral antigens, or microbial antigens), those skilled in the art can select suitable antibody useful in the bio-conjugation process of the present disclosure. In some embodiments, the antibody is an antibody which binds to one or more tumor-associated antigens or cell-surface receptors as described elsewhere herein. The antibody may include, but not limited to, a monoclonal antibody, a polyclonal antibody, a mono-specific antibody, a multispecific antibody, or an antibody derivate.

In an embodiment, the antibody is a monoclonal antibody. In another embodiment, the antibody is a human antibody, a humanized antibody or a chimeric antibody. In a further embodiment, the antibody is an antibody fragment, e.g., a Fv, Fab, Fab', scFv, diabody, or F(ab')2 fragment. In another embodiment, the antibody is a substantially full-length antibody, e.g., an IgG1 antibody, IgG4 antibody or other antibody class or isotype as defined herein. In a specific embodiment, the antibody is an IgG1 antibody.

In some other embodiments, the antibody is selected from Herceptin®(trastuzumab), Rituxan®(rituximab), Erbitux® (cetuximab), or antibodies against any one of the following antigens: BMPR1B, E16, STEAP1, MUC16, MPF, Napi2b, Sema 5b, PSCA hlg, ETBR, MSG783, STEAP2, TrpM4, CRIPTO, CD21, CD79b, FcRH2, HER2, NCA, MDP, IL20Ra, Brevican, EphB2R, ASLG659, PSCA, GEDA, BAFF-R, CD22, CD79a, CXCR5, HLA-DOB, P2X5, CD72, LY64, FcRH1, FcRH5, TENB2, PMEL17, TMEFF1, GDNF-Ra1, Ly6E, TMEM46, Ly6G6D, LGR5, RET, Ly6K, GPR19, GPR54, ASPHD1, Tyrosinase, TMEM118, GPR172A, CD33 and CLL-1.

Useful Polyclonal antibody is a heterogeneous population of antibody molecules derived from the sera of immunized animals. Various procedures well known in the art may be used for the production of polyclonal antibodies to an antigen-of-interest. For example, for the production of polyclonal antibodies, various host animals can be immunized by injection with an antigen of interest or derivative thereof, including but not limited to rabbits, mice, rats, and guinea pigs.

Useful monoclonal antibody is a homogeneous population of antibodies to a particular antigen (e.g., a cancer cell antigen, a viral antigen, a microbial antigen covalently linked to a second molecule). A monoclonal antibody (mAb) to an antigen-of-interest can be prepared by using any technique known in the art which provides for the production of antibody molecules by continuous cell lines in culture. These include, but are not limited to, the hybridoma technique originally described by Kohler and Milstein (1975, Nature 256, 495497), the human-B cell hybridoma technique (Kozbor et al., 1983, Immunology Today 4: 72), and the EBV-hybridoma technique (Cole et al., 1985, Monoclonal Antibodies and Cancer Therapy, Alan R. Liss, Inc., pp. 77-96). Such antibodies may be of any immunoglobulin class including IgG, IgM, IgE, IgA, and IgD and any subclass thereof. The hybridoma producing the mAbs of use in this invention may be cultivated in vitro or in vivo.

Useful monoclonal antibodies include, but are not limited to, human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80, 7308-7312; Kozbor et al., 1983, Immunology Today 4, 72-79; and Olsson et al., 1982, Meth. Enzymol. 92, 3-16).

There are various methods for producing a human antibody in the art. For example, a human antibody may be prepared by administering an immunogen to a transgenic animal that has been modified to produce intact human antibodies or intact antibodies with human variable regions in response to antigenic challenge. For review of methods for obtaining human antibodies from transgenic animals, see Lonberg, Nat. Biotech. 23: 1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology.

Human antibodies can also be made by hybridoma-based methods. Human myeloma and mouse-human heteromyeloma cell lines for the production of human monoclonal antibodies have been described (See, e.g., Kozbor J. Immunol, 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991)). Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are well known in the art.

Additionally, recombinant antibodies, such as chimeric and humanized monoclonal antibodies, comprising both human and non-human portions, which can be made using standard recombinant DNA techniques, are useful Ligands. A chimeric antibody is a molecule in which different portions are derived from different animal species, such as those having a variable region derived from a murine monoclonal and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 184,187; European Patent Publication No. 171,496; European Patent Publication No. 173,494; International Publication No. WO 86/01533; U.S. Pat. No. 4,816,567; European Patent Publication No. 125,023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al. (1988) Science 239:1534; and Beidler et al., 1988, J. Immunol. 141:4053-4060; each of which is incorporated herein by reference in its entirety.

In a specific embodiment, known antibodies for the treatment or prevention of cancer are used in the invention. Antibodies immunospecific for a cancer cell antigen can be obtained commercially or produced by any method known to one of skill in the art, such as, e.g., chemical synthesis or recombinant expression techniques. The nucleotide sequence encoding antibodies immunospecific for a cancer cell antigen can be obtained, e.g. from the GenBank database or a database like it, the literature publications, or by routine cloning and sequencing. Examples of antibodies available for the treatment of cancer include, but are not limited to, Herceptin®(Trastuzumab; Genentech, CA) which is a humanized anti-HER2 monoclonal antibody for the treatment of patients with metastatic breast cancer (Stebbing, J., Copson, E., and O'Reilly, S. "Herceptin®(trastuzamab) in advanced breast cancer" Cancer Treat Rev. 26, 287-90, 2000); Rituxan®(rituximab; Genentech) which is a chimeric anti-CD20 monoclonal antibody for the treatment of patients with non-Hodgkin's lymphoma; Erbitux®(cetuximab; Merck) which is an IgG1 monoclonal antibody against EGF receptors and used for the treatment of colorectal cancer; OvaRex (AltaRex Corporation, MA) which is a murine antibody for the treatment of ovarian cancer; Panorex (Glaxo Wellcome, NC) which is a murine IgG2a antibody for the treatment of colorectal cancer; BEC2 (Imclone Systems Inc., NY) which is murine IgG antibody for the treatment of lung cancer; IMC-C225 (Imclone Systems Inc., NY) which is a chimeric IgG antibody for the treatment of head and neck cancer; Vitaxin (MedImmune, Inc., MD) which is a humanized antibody for the treatment of sarcoma; Campath I/H (Leukosite, MA) which is a humanized IgG1 antibody for the treatment of chronic lymphocytic leukemia (CLL); Smart MI95 (Protein Design Labs, Inc., CA) which is a humanized IgG antibody for the treatment of acute myeloid leukemia (AML); LymphoCide (Immunomedics, Inc., NJ) which is a humanized IgG antibody for the treatment of non-Hodgkin's lymphoma; Smart ID10 (Protein Design Labs, Inc., CA) which is a humanized antibody for the treatment of non-Hodgkin's lymphoma; Oncolym (Techniclone, Inc., CA) which is a murine antibody for the treatment of non-Hodgkin's lymphoma; Allomune (BioTransplant, CA) which is a humanized anti-CD2 mAb for the treatment of Hodgkin's Disease or non-Hodgkin's lymphoma; anti-VEGF (Genentech, Inc., CA) which is humanized antibody for the treatment of lung and colorectal cancers; CEAcide (Immunomedics, NJ) which is a humanized anti-CEA antibody for the treatment of colorectal cancer; IMC-1C11 (ImClone Systems, NJ) which is an anti-KDR chimeric antibody for the treatment of colorectal cancer, lung cancers, and melanoma; and Cetuximab (ImClone, NJ) which is an anti-EGFR chimeric antibody for the treatment of epidermal growth factor positive cancers.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), MAGE-1 (carcinomas), MAGE-2 (carcinomas), MAGE-3 (carcinomas), MAGE 4 (carcinomas), anti-transferrin receptor (carcinomas), p97 (melanoma), MUC1-KLH (breast cancer), CEA (colorectal), gp100 (melanoma), MART1 (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific useful antibodies include, but are not limited to, BR96 mAb (Trail, P. A., Willner, D., Lasch, S. J., Henderson, A. J., Hofstead, S. J., Casazza, A. M., Firestone, R. A., Hellstrom, I., Hellstrom, K. E., "Cure of Xenografted Human Carcinomas by BR96-Doxorubicin Immunoconjugates" Science 1993, 261, 212-215), BR64 (Trail, Pa., Willner, D, Knipe, J., Henderson, A. J., Lasch, S. J., Zoeckler, M. E., Trailsmith, M. D., Doyle, T. W., King, H. D., Casazza, A. M., Braslawsky, G. R., Brown, J. P., Hofstead, S. J., Greenfield, Ill. S., Firestone, R. A., Mosure, K., Kadow, D. F., Yang, M. B., Hellstrom, K E., and Hellstrom, I. "Effect of Linker Variation on the Stability, Potency, and Efficacy of Carcinoma-reactive BR64-Doxorubicin Immunoconjugates" Cancer Research 1997, 57, 100-105), mAbs against the CD40 antigen, such as S2C6 mAb (Francisco, J. A., Donaldson, K. L., Chace, D., Siegall, C. B., and Wahl, A. F. "Agonistic properties and in vivo antitumor activity of the anti-CD-40 antibody, SGN-14" Cancer Res. 2000, 60, 3225-3231), mAbs against the CD70 antigen, such as 1F6 mAb, and mAbs against the CD30 antigen, such as AC10 (Bowen, M. A., Olsen, K. J., Cheng, L., Avila, D., and Podack, E. R. "Functional effects of CD30 on a large granular lymphoma cell line YT" J. Immunol., 151, 5896-5906, 1993). Many other internalizing antibodies that bind to tumor associated antigens can be used in this invention, and have been reviewed (Franke, A. E., Sievers, E. L., and Scheinberg, D. A., "Cell surface receptor-targeted therapy of acute myeloid leukemia: a review" Cancer Biother Radiopharm. 2000, 15,459-76; Murray, J. L., "Monoclonal antibody treatment of solid tumors: a coming of age" Semin Oncol. 2000, 27, 64-70; Breitling, F., and Dubel, S., Recombinant Antibodies, John Wiley, and Sons, New York, 1998).

In another specific embodiment, known antibodies for the treatment or prevention of an autoimmune disease are used in accordance with the process of the disclosure. Antibodies immunospecific for an antigen of a cell that is responsible for producing autoimmune antibodies can be obtained from any organization (e.g., a university scientist or a company such as Genentech) or produced by any method known to one of skill in the art such as, e.g., chemical synthesis or recombinant expression techniques. In another embodiment, useful ligand antibodies that are immunospecific for the treatment of autoimmune diseases include, but are not limited to, Anti-Nuclear Antibody; Anti dsDNA; Anti ssDNA, Anti Cardiolipin Antibody IgM, IgG; Anti Phospholipid Antibody IgK, IgG; Anti SM Antibody; Anti Mitochondrial Antibody; Thyroid Antibody; Microsomal Antibody, Thyroglobulin Antibody, Anti SCL-70; Anti-Jo; Anti-U1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody.

In another specific embodiment, useful antibodies that are immunospecific for a viral or a microbial antigen are monoclonal antibodies. For instance, antibodies that are immunospecific for a viral antigen or microbial antigen may be humanized or human monoclonal antibodies. As used herein, the term "viral antigen" includes, but is not limited to, any viral peptide, polypeptide protein (e.g. HIV gp120, HIV nef, RSV F glycoprotein, influenza virus neuraminidase, influenza virus hemagglutinin, HTLV tax, herpes simplex virus glycoprotein (e.g. gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Antibodies immunospecific for a viral or microbial antigen can be obtained commercially, for example, from Genentech (San Francisco, Calif.) or produced by any method known to one of skill in the art such as, e.g., chemical synthesis or recombinant expression techniques. The nucleotide sequence encoding antibodies that are immunospecific for a viral or microbial antigen can be obtained, e.g., from the GenBank database or a database like it, the literature publications, or by routine cloning and sequencing.

In a specific embodiment, useful antibodies are those that are useful for the treatment or prevention of viral or microbial infection. Examples of antibodies available useful for the treatment of viral infection or microbial infection include, but are not limited to, SYNAGIS (MedImmune, Inc., MD) which is a humanized anti-respiratory syncytial virus (RSV) monoclonal antibody useful for the treatment of patients with RSV infection; PRO542 (Progenics) which is a CD4 fusion antibody useful for the treatment of HIV infection; OSTAVIR (Protein Design Labs, Inc., CA) which is a human antibody useful for the treatment of hepatitis B virus; PROTVIR (Protein Design Labs, Inc., CA) which is a humanized IgG1 antibody useful for the treatment of cytomegalovirus (CMV); and anti-LPS antibodies.

Other antibodies useful in the treatment of infectious diseases include, but are not limited to, antibodies against the antigens from pathogenic strains of bacteria (*Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococcus aureus, Vibrio colerae, Escherichia coli, Pseudomonas aeruginosa, Campylobacter* (*Vibrio*) *fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma* spp., *Rickettsia prowazeki, Rickettsia tsutsugumushi, Clamydia* spp.); pathogenic fungi (*Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or *Helminiths* (*Enterobius vermicularis, Trichuris trichiura, Ascaris lumbricoides, Trichinella spiralis, Strongyloides stercoralis, Schistosoma japonicum, Schistosoma mansoni, Schistosoma haematobium*, and hookworms).

Other antibodies useful in this invention for treatment of viral disease include, but are not limited to, antibodies against antigens of pathogenic viruses, including as examples and not by limitation: Poxyiridae, Herpesviridae, Herpes Simplex virus 1, Herpes Simplex virus 2, Adenoviridae, Papovaviridae, Enteroviridae, Picomaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus.

The antibodies suitable for use in the bio-conjugation process provided herein can be produced by any method known in the art for the synthesis of antibodies, in particular, by chemical synthesis or by recombinant expression, and, for example, are produced by recombinant expression techniques.

As for the payload bearing reactive group to be conjugated to the selected antibody, it generally has a format of drug-linker. There are no specific limitations to the drug and linker which can be used in the bio-conjugation process of the present disclosure, as long as the drug molecule has an antitumor, antiviral or antimicrobial effect and contains at least one substituted group or a partial structure allowing connection to a linker structure, and the linker contains at least two reactive groups, one of which can covalently bond a drug molecule and the other of which can covalently couple to an antibody.

Depending on the desired drug and selected linker, those skilled in the art can select suitable method for coupling them together. For example, some conventional coupling methods, such as amine coupling methods, may be used to form the desired drug-linker complex which still contains reactive groups for conjugating to the antibodies through covalent linkage. A drug-maleimide complex (i.e., maleimide linking drug) is taken as an example of the payload bearing reactive group in the present disclosure.

In an embodiment, the drug may include, but not limited to, cytotoxic reagents, such as chemo-therapeutic agents, immunotherapeutic agents and the like, antiviral agents or antimicrobial agents. In an embodiment, the drug to be conjugated with an antibody may be selected from, but not limited to, MMAE (monomethyl auristatin E), MMAD (monomethyl auristatin D), MMAF (monomethyl auristatin F), and the like.

Most common reactive group capable of bonding to thiol group in ADC preparation is maleimide. Additionally, organic bromides, iodides also are frequently used.

Drug loading is represented by the number of drug moieties per antibody in a molecule of ADC. For some antibody-drug conjugates, the drug loading may be limited by the number of attachment sites on the antibody. For example, where the attachment is a cysteine thiol, as in certain exemplary embodiments described herein, the drug loading may range from 0 to 8 drug moieties per antibody. In certain embodiments, higher drug loading, e.g. p≥5, may cause aggregation, insolubility, toxicity, or loss of cellular permeability of certain antibody-drug conjugates. In certain embodiments, the average drug loading for an antibody-drug conjugate ranges from 1 to about 8; from about 2 to about 6; or from about 3 to about 5. Indeed, it has been shown that for certain antibody-drug conjugates, the optimal ratio of drug moieties per antibody may be 4 (see, e.g., WO2013190292).

It is to be understood that where more than one nucleophilic group reacts with a drug, then the resulting product is a mixture of antibody-drug conjugate compounds with a distribution of one or more drug moieties attached to an antibody. The average number of drugs per antibody may be calculated from the mixture by a dual ELISA antibody assay, which is specific for antibody and specific for the drug. Individual antibody-drug conjugate molecules may be identified in the mixture by mass spectroscopy and separated by HPLC, e.g. hydrophobic interaction chromatography (see, e.g., McDonagh et al. (2006) Prot. Engr. Design & Selection 19(7):299-307; Hamblett et al. (2004) Clin. Cancer Res. 10:7063-7070; Hamblett, K. J., et al. "Effect of drug loading on the pharmacology, pharmacokinetics, and toxicity of an anti-CD30 antibody-drug conjugate", Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates", Abstract No. 627, American Association for Cancer Research, 2004 Annual Meeting, Mar. 27-31, 2004, Proceedings of the AACR, Volume 45, March 2004). In certain embodiments, a homogeneous antibody-drug conjugate with a single loading value may be isolated from the conjugation mixture by electrophoresis or chromatography.

Improving homogeneity of ADCs requires isolation of ADC with certain drug loading or selective attachment of drug moieties to an antibody in the conjugation process. However, the isolation of ADC with certain drug loading will result in complex manipulation and high cost. With a conjugation process using the same steps without the addition of transition metal ions in step (a) as a negative control (see U.S. Pat. No. 7,659,241B2), the inventors successfully demonstrated that transition metal ions were the key factor responsible for higher level of D4 and lower level of D0, D6 and D8 in the resultant ADCs. Furthermore, the inventors also confirmed this new process generates ADC products with a high Fab preference. By using the process of the present disclosure to produce antibody-drug conjugates, the homogeneity of the antibody-drug conjugates is higher than those produced by conventional conjugation processes. Specifically, in the ADCs prepared by the process of the present disclosure, the content of D0+D8 is less than 10 wt % and the content of D6 is less than 10 wt %. Moreover, the content of D4 is generally more than 65 wt %, and, for example, more than 70 wt %, while the content D4 is normally less than 40 wt % in the ADCs prepared by conventional conjugation processes.

In an embodiment, the resultant antibody-drug conjugates are recovered by any suitable purification method, such as using a de-salting column, size exclusion chromatography, ultrafiltration, dialysis, UF-DF, and the like.

Antibody-Drug Conjugates with Improved Homogeneity

In a second aspect, the present disclosure relates to the antibody-drug conjugates with improved homogeneity prepared by the process of the first aspect. The improved homogeneity of ADC is represented by high level of D4 in the resultant ADCs.

In an embodiment, the homogeneity of the antibody-drug conjugates generated by the process of the first aspect is measured, and compared with the homogeneity of corresponding control antibody-drug conjugates generated by conventional conjugation processes.

Figure 5:
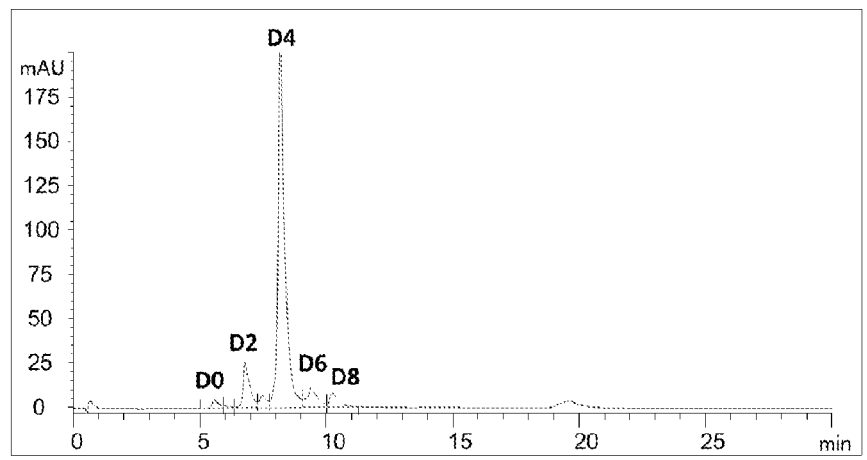
FIG. 5. HIC of Rituxan®(rituximab) MMAE conjugate prepared by using the process of the disclosure.

Various analytical methods can be used to determine the yields and isomeric mixtures of the antibody-drug conjugates. For example, in one embodiment, HIC is the analytical method used to determine yields and isomeric mixtures from resultant antibody-drug conjugates (e.g., for D4 conjugates). This technique is able to separate antibodies loaded with various numbers of drugs. The drug loading level can be determined based on the ratio of absorbances, e.g., at 250 nm and 280 nm. For example, if a drug can absorb at 250 nm while the antibody absorbs at 280 nm. The 250/280 ratio therefore increases with drug loading. Using the bio-conjugation process described herein, generally antibodies with even numbers of drugs were observed to be conjugated to the antibody since reduction of disulfides yields even numbers of free cysteine thiols. FIGS. 1, 3 and 5 show HIC separations for
Herceptin®(trastuzumab) MC-VC-PAB-MMAE conjugate, Rituxan®(rituximab) MC-VC-PAB-MMAE conjugate and Erbitux®(cetuximab) MC-VC-PAB-MMAE conjugate prepared by the process of the present disclosure, respectively, and FIGS. 2, 4 and 6 show HIC separations for the counterparts prepared by the conventional conjugation process (without transitional metal ions), respectively. Table 1 shows the product distribution summarized from HIC figures, clearly indicating that the content of D4 is 73.5 wt % (FIG. 1), 75 wt % (FIG. 3), and 77.9 wt % (FIG. 5), respectively.

As compared with corresponding control antibody-drug conjugates generated by conventional conjugation processes, the antibody-drug conjugates generated by the process of the first aspect have improved homogeneity, which is represented by the increased content of D4 in the resultant ADCs. In an embodiment, as shown in Table 1, the content of D4 in the antibody-drug conjugates generated by the process of the present disclosure is higher than 65 wt %, for example, higher than 70 wt %, higher than 77 wt %, whereas the content of D4 in the antibody-drug conjugates generated by conventional conjugation processes is usually less than 40 wt %.

A Pharmaceutical Composition

In a third aspect, the present disclosure relates to a pharmaceutical composition comprising an effective amount of the ADCs with improved homogeneity prepared by the process of the first aspect and a pharmaceutically acceptable carrier or vehicle. The compositions are suitable for veterinary or human administration.

The compositions of the present invention can be in any form that allows for the composition to be administered to an animal. For example, the composition can be in the form of a solid, liquid or gas (aerosol). Typical routes of administration include, without limitation, oral, topical, parenteral, sublingual, rectal, vaginal, ocular, and intranasal. Parenteral administration includes subcutaneous injections, intravenous, intramuscular, intrasternal injection or infusion techniques. For example, the compositions are administered parenterally. Pharmaceutical compositions of the invention can be formulated so as to allow ADCs of the invention to be bioavailable upon administration of the composition to an animal. Compositions can take the form of one or more dosage units, where for example, a tablet can be a single dosage unit, and a container of ADCs of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the ADCs of the Invention, the manner of administration, and the composition employed.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a pharmaceutical composition provided herein decreases oxidation of the polypeptide complex or the bispecific polypeptide complex. This reduction in oxidation prevents or reduces loss of binding affinity, thereby improving protein stability and maximizing shelf-life. Therefore, in certain embodiments, compositions are provided that comprise the polypeptide complex or the bispecific polypeptide complex disclosed herein and one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, non-aqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or non-aqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving the ADCs as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agents. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the ADCs provided herein or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Additionally, the antibody-drug conjugates or the pharmaceutical composition may be manufactured into a kit, including an insert which indicates the information for the application, such as the indications, the amount in use, the route to be administrated, and the like.

Use of the Antibody-Drug Conjugates with Improved Homogeneity

In a fourth aspect, the present disclosure relates to the use of the antibody-drug conjugates with improved homogeneity prepared by the process of the first aspect in the manufacture of a pharmaceutical composition or a kit for treating a condition or disorder in a subject.

The subject may be a mammal, for example, a human.

The condition or disorder to be treated may be a tumor, cancer, autoimmune disease, or infectious disease. In specific embodiments, the infectious disease may be viral or microbial infection.

In a fifth aspect, the present disclosure also relates to a method for treating a subject having a condition or disorder, comprising: administrating a therapeutically effective amount of the ADCs with improved homogeneity prepared by the process of the first aspect or a therapeutically effective amount of the pharmaceutical composition comprising the ADCs with improved homogeneity prepared by the process of the first aspect to a subject in need thereof, thereby treating or preventing the condition or disorder.

In certain embodiments, the subject has been identified as having a condition or disorder likely to respond to the ADCs provided herein.

The subject may be a mammal, for example, a human.

The condition or disorder to be treated may be a tumor, cancer, autoimmune disease, or infectious disease. In specific embodiments, the infectious disease may be viral or microbial infection.

The therapeutically effective amount of the ADCs provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements.

In certain embodiments, the ADCs or pharmaceutical composition provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the ADCs or pharmaceutical composition provided herein are administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The ADCs or pharmaceutical composition provided herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In certain embodiments, the condition or disorder treated by the ADCs or pharmaceutical composition provided herein is cancer or a cancerous condition, autoimmune disease or infectious disease.

The cancer may be antigen positive carcinomas including those of the lung, breast, colon, ovaries, and pancreas, for example, the cancers associated with tumor-associated antigens listed in (1)-(53) under the heading of "TUMOR-ASSOCIATED ANTIGENS (TAA)".

Other particular types of cancers that can be treated with the ADCs or pharmaceutical composition provided herein include, but are not limited to, solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma; blood-borne cancers, including but not limited to: acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma; Lymphomas: B cell lymphoma, optionally Hodgkin lymphoma or non-Hodgkin lymphoma, wherein the non-Hodgkin lymphoma comprises: Diffuse large B-cell lymphoma (DLBCL), Follicular lymphoma, Marginal zone B-cell lymphoma (MZL), Mucosa-Associated Lymphatic Tissue lymphoma (MALT), Small lymphocytic lymphoma (chronic lymphocytic leukemia, CLL), or Mantle cell lymphoma (MCL), Acute Lymphoblastic Leukemia (ALL), or Waldenstrom's Macroglobulinemia (WM).

The autoimmune disease may include, but not limited to, Active Chronic Hepatitis, Addison's Disease, Allergic Alveolitis, Allergic Reaction, Allergic Rhinitis, Alport's Syndrome, Anaphlaxis, Ankylosing Spondylitis, Anti-phosholipid Syndrome, Arthritis, Ascariasis, Aspergillosis, Atopic Allergy, Atropic Dermatitis, Atropic Rhinitis, Behcet's Disease, Bird-Fancier's Lung, Bronchial Asthma, Caplan's Syndrome, Cardiomyopathy, Celiac Disease, Chagas' Disease, Chronic Glomerulonephritis, Cogan's Syndrome, Cold Agglutinin Disease, Congenital Rubella Infection, CREST Syndrome, Crohn's Disease, Cryoglobulinemia, Cushing's Syndrome, Dermatomyositi, Discoid Lupus, Dressler's Syndrome, Eaton-Lambert Syndrome, Echovirus Infection, Encephalomyelitis, Endocrine opthalmopathy, Epstein-Barr Virus Infection, Equine Heaves, Erythematosis, Evan's Syndrome, Felty's Syndrome, Fibromyalgia, Fuch's Cyclitis, Gastric Atrophy, Gastrointestinal Allergy, Giant Cell Arteritis, Glomerulonephritis, Goodpasture's Syndrome, Graft v. Host Disease, Graves' Disease, Guillain-Barre Disease, Hashimoto's Thyroiditis, Hemolytic Anemia, Henoch-Schonlein Purpura, Idiopathic Adrenal Atrophy, Idiopathic Pulmonary Fibrosis, IgA Nephropathy, Inflammatory Bowel Diseases, Insulin-dependent Diabetes Mellitus, Juvenile Arthritis, Juvenile Diabetes Mellitus (Type I), Lambert-Eaton Syndrome, Laminitis, Lichen Planus, Lupoid Hepatitis, Lupus, Lymphopenia, Meniere's Disease, Mixed Connective Tissue Disease, Multiple Sclerosis, Myasthenia Gravis, Pernicious Anemia, Polyglandular Syndromes, Presenile Dementia, Primary Agammaglobulinemia, Primary Biliary Cirrhosis, Psoriasis, Psoriatic Arthritis, Raynauds Phenomenon, Recurrent Abortion, Reiter's Syndrome, Rheumatic Fever, Rheumatoid Arthritis, Sampter's Syndrome, Schistosomiasis, Schmidt's Syndrome, Scleroderma, Shulman's Syndrome, Sjorgen's Syndrome, Stiff-Man Syndrome, Sympathetic Ophthalmia, Systemic Lupus Erythematosis, Takayasu's Arteritis, Temporal Arteritis, Thyroiditis, Thrombocytopenia, Thyrotoxicosis, Toxic Epidermal Necrolysis, Type B Insulin Resistance, Type I Diabetes Mellitus, Ulcerative Colitis, Uveitis, Vitiligo, Waldenstrom's Macroglobulemia, Wegener's Granulomatosis.

Particular types of infectious diseases that can be treated with the ADCs or pharmaceutical composition of the disclosure include, but are not limited to, Bacterial Diseases: Diptheria, Pertussis, Occult Bacteremia, Urinary Tract Infection, Gastroenteritis, Cellulitis, Epiglottitis, Tracheitis, Adenoid Hypertrophy, Retropharyngeal Abcess, Impetigo, Ecthyma, Pneumonia, Endocarditis, Septic Arthritis, Pneumococcal, Peritonitis, Bactermia, Meningitis, Acute Purulent Meningitis, Urethritis, Cervicitis, Proctitis, Pharyngitis, Salpingitis, Epididymitis, Gonorrhea, Syphilis, Listeriosis, Anthrax, Nocardiosis, *Salmonella*, Typhoid Fever, Dysentery, Conjuntivitis, Sinusitis, Brucellosis, Tullaremia, Cholera, Bubonic Plague, Tetanus, Necrotizing Enteritis, Actinomycosis, Mixed Anaerobic Infections, Syphilis, Relapsing Fever, Leptospirosis, Lyme Disease, Rat Bite Fever, Tuberculosis, Lymphadenitis, Leprosy, *Chlamydia*, Chlamydial Pneumonia, Trachoma, Inclusion Conjunctivitis; Systemic Fungal Diseases: Histoplamosis, Coccicidiodomycosis, Blastomycosis, Sporotrichosis, Cryptococcis, Systemic Candidiasis, Aspergillosis, Mucormycosis, Mycetoma, Chromomycosis; Rickettsial Diseases: Typhus, Rocky Mountain Spotted Fever, Ehrlichiosis, Eastern Tick-Bome Rickettsioses, Rickettsialpox, Q Fever, Bartonellosis; Parasitic Diseases: Malaria, Babesiosis, African Sleeping Sickness, Chagas' Disease, Leishmaniasis, Dum-Dum Fever, Toxoplasmosis, Meningoencephalitis, Keratitis, Entamebiasis, Giardiasis, Cryptosporidiasis, Isosporiasis, Cyclosporiasis, Microsporidiosis, Ascariasis, Whipworm Infection, Hookworm Infection, Threadworm Infection, Ocular Larva Migrans, Trichinosis, Guinea Worm Disease, Lymphatic Filariasis, Loiasis, River Blindness, Canine Heartworm Infection, Schistosomiasis, Swimmer's Itch, Oriental Lung Fluke, Oriental Liver Fluke, Fascioliasis, Fasciolopsiasis, Opisthorchiasis, Tapeworm Infections, Hydatid Disease, Alveolar Hydatid Disease; Viral Diseases: Measles, Subacute sclerosing panencephalitis, Common Cold, Mumps, Rubella, Roseola, Fifth Disease, Chickenpox, Respiratory syncytial virus infection, Croup, Bronchiolitis, Infectious Mononucleosis, Poliomyelitis, Herpangina, Hand-Foot-and-Mouth Disease, Bornholm Disease, Genital Herpes, Genital Warts, Aseptic Meningitis, Myocarditis, Pericarditis, Gastroenteritis, Acquired Immunodeficiency Syndrome (AIDS), Rey's Syndrome, Kawasaki Syndrome, Influenza, Bronchitis, Viral "Walking" Pneumonia, Acute Febrile Respiratory Disease, Acute pharyngoconjunctival fever, Epidemic keratoconjunctivitis, Herpes Simplex Virus 1 (HSV-1), Herpes Simples Virus 2 (HSV-2), Shingles, Cytomegalic Inclusion Disease, Rabies, Progressive Multifocal Leukoencephalopathy, Kuru, Fatal Familial Insomnia, Creutzfeldt-Jakob Disease, Gerstmann-Straussler-Scheinker Disease, Tropical Spastic Paraparesis, Western Equine Encephalitis, California Encephalitis, St. Louis Encephalitis, Yellow Fever, Dengue, Lymphocytic choriomeningitis, Lassa Fever, Hemorrhagic Fever, Hantvirus Pulmonary Syndrome, Marburg Virus Infections, Ebola Virus Infections, Smallpox.

In one embodiment, the present disclosure includes a method for treating disease or disorder in a subject, comprising administering to the subject an effective amount of ADCs or pharmaceutical composition provided herein and another therapeutic agent.

In some embodiments, the therapeutic agent is an anticancer agent. Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel.

In some embodiments, the therapeutic agent is an anti-autoimmune disease agent. Suitable anti-autoimmune disease agents include, but are not limited to, cyclosporine, cyclosporine A, mycophenylate mofetil, Sirolimus, tacrolimus, etanercept, prednisone, azathioprine, methotrexate cyclophosphamide, prednisone, aminocaproic acid, chloroquine, hydroxychloroquine, hydrocortisone, dexamethasone, chlorambucil, DHEA, danazol, bromocriptine, meloxican, and infliximab.

In some embodiments, the therapeutic agent is anti-infectious disease agent. In one embodiment, the anti-infectious disease agent is, but not limited to, antibacterial agents: [beta]-Lactam Antibiotics: Penicillin G, Penicillin V, Cloxacilliin, Dicloxacillin, Methicillin, Nafcillin, Oxacillin, Ampicillin, Amoxicillin, Bacampicillin, Azlocillin, Carbenicillin, Mezlocillin, Piperacillin, Ticarcillin; Aminoglycosides: Amikacin, Gentamicin, Kanamycin, Neomycin, Netilmicin, Streptomycin, Tobramycin; Macrolides: Azithromycin, Clarithromycin, Erythromycin, Lincomycin, Clindamycin; Tetracyclines: Demeclocycline, Doxycycline, Minocycline, Oxytetracyclinem, Tetracycline; Quinolones: Cinoxacin, Nalidixic Acid; Fluoroquinolones: Ciprofloxacin, Enoxacin, Grepafloxacin, Levofloxacin, Lomefloxacin, Norfloxacin, Ofloxacin, Sparfloxacin, Trovafloxicin; Polypeptides: Bacitracin, Colistin, Polymyxin B; Sulfonamides: Sulfisoxazole, Sulfamethoxazole, Sulfadiazine, Sulfamethizole, Sulfacetamide; Miscellaneous Antibacterial Agents: Trimethoprim, Sulfamethazole, Chloramphenicol, Vancomycin, Metronidazole, Quinupristin, Dalfopristin, Rifampin, Spectinomycin, Nitrofurantoin; Antiviral Agents: General Antiviral Agents: Idoxuradine, Vidarabine, Trifluridine, Acyclovir, Famcicyclovir, Pencicyclovir, Valacyclovir, Gancicyclovir, Foscamet, Ribavirin, Amantadine, Rimantadine, Cidofovir, Antisense Oligonucleotides, Immunoglobulins, Inteferons; Drugs for HIV infection: Zidovudine, Didanosine, Zalcitabine, Stavudine, Lamivudine, Nevirapine, Delavirdine, Saquinavir, Ritonavir, Indinavir, Nelfinavir.

In a specific embodiment, in order to demonstrate the process of the disclosure, three antibodies, Herceptin® (trastuzumab), Rituxan®(rituximab) and Erbitux®(cetuximab (produced in WuXi Biologics, according to the published corresponding protein sequences, via standard method for preparing monoclonal antibodies, respectively), were chosen to perform conjugation with MC-VC-PAB-MMAE (commercially available from Lenena, biopharma). A typical conjugation experiment procedure in a one-pot manner is as follows: firstly, ZnCl2 (0.04 mM) and TCEP (0.08 mM) were subsequently added to a solution of a solution of an antibody (i.e., one selected from Herceptin® (trastuzumab), Rituxan®(rituximab) or Erbitux®(cetuximab), 0.02 mM, in phosphate buffer, pH7, 20 mM), to obtain a reaction mixture. The reaction mixture was allowed to stay at 4° C. overnight. Then MC-VC-PAB-MMAE (0.12 mM) in DMA (Dimethylacetamide, commercially available from Aldrich Sigma) was introduced and the reaction was continued for 2 h at 4° C.; after that, cysteine (0.08 mM) was added to deplete excessive MC-VC-PAB-MMAE; subsequently, EDTA (0.08 mM) was added to trap Zn2+ and DHAA (commercially available from Aldrich Sigma) (0.16 mM) was added to oxidize the excessive thiol groups. Finally, the reaction mixture was subjected to purification using de-salting column and the drug/antibody ratio (DAR) and product distribution were analyzed using HIC-HPLC. The results were shown in the Table 1 and FIGS. 1-6.

Example 2. Preparation of Rituxan®(Rituximab) MC-VC-PAB-MMAE Conjugate by Using the Process of the Present Disclosure and Homogeneity Thereof The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Now the present disclosure will be illustrated in detail with reference to the following examples. However, those skilled in the art should understand that, the following examples are only provided for illustration, but not intended to limit the present disclosure in any way.

Example 1. Preparation of Herceptin-MC-VC-PAB-MMAE Conjugate by Using the Process of the Present Disclosure and Homogeneity Thereof The Herceptin-MC-VC-PAB-MMAE conjugate is prepared in a one-pot reaction:
(1) $ZnCl_2$ (0.04 mM) and TCEP (0.08 mM) were added to a solution of Herceptin (produced in WuXi Biologics, according to the published corresponding protein sequences, via standard method for preparing monoclonal antibodies, 0.02 mM, in phosphate buffer, pH7, 20 mM) and the reaction mixture was allowed to stay at 4° C. overnight;
(2) MC-VC-PAB-MMAE (commercially available from Lenena, biopharma, 0.12 mM) in DMA (Dimethylacetamide, commercially available from Aldrich Sigma) was introduced and the reaction was continued at 4° C. for 2 h;
(3) cysteine (0.08 mM) was added to deplete excessive MC-VC-PAB-MMAE;
(4) EDTA (0.08 mM) was added to trap $Zn^{2+}$ and DHAA (commercially available from Aldrich Sigma, 0.16 mM) was added to oxidize the excessive thiol groups;
(5) the reaction mixture was subjected to purification using a de-salting column (type: 40K, 0.5 mL, REF: 87766, Lot #SJ251704, Manufacturer: Thermo).

As a control, the reaction is performed in the same steps in the presence of 0.05 mM TCEP but without $ZnCl_2$.

Homogeneity assays. Finally, the drug/antibody ratio (DAR) and product distribution were analyzed using HIC-HPLC. Purification of D0, D2, D4, D6 and D8 by hydrophobic interaction chromatography (HIC) was performed on a Toyopearl phenyl 650M HIC column (Tosoh Biosciences, Montgomeryville, PA) at a flow rate of 10 mL/min at ambient temperature. The column size was 1 mL per 7.5 mg of ADCs. Solvent A was 2.0 M NaCl and 50 mM sodium phosphate pH 7. Solvent B was 80% v/v 50 mM sodium phosphate pH 7 and 20% v/v acetonitrile. The column was previously equilibrated with 5 column volumes of solvent A. the ADCs were mixed with 0.67 volume of 5 M NaCl (2.0 M final) and applied to the column. D0 was not retained by the column. The different drug loaded species were eluted by sequential step gradients: D2 was eluted with 35% solvent B, D4 was eluted with 70% solvent B, D6 was eluted with 95% solvent B, and D8 was eluted with 100% solvent B.

The results were shown in Table 1 and FIG. 1-2.

TABLE 1

| Sample Name | D0 (wt %) | D2 (wt %) | D4 (wt %) | D6 (wt %) | D8 (wt %) | HIC-DAR |
|---|---|---|---|---|---|---|
| Herceptin-MMAE (with $ZnCl_2$, FIG. 1) | 2.3 | 10.1 | 73.5 | 7.7 | 6.3 | 4.1 |
| Herceptin-MMAE (without $ZnCl_2$, FIG. 2) | 6.2 | 28.4 | 38.3 | 20.7 | 6.4 | 3.9 |

Example 2. Preparation of Rituxan-MC-VC-PAB-MMAE Conjugate by Using the Process of the Present Disclosure and Homogeneity Thereof The Rituxan®(rituximab) MC-VC-PAB-MMAE conjugate is prepared in a one-pot reaction:
(1) ZnCl2 (0.04 mM) and TCEP (0.08 mM) were subsequently added to a solution of Rituxan®(rituximab) (produced in WuXi Biologics, according to the published corresponding protein sequences, via standard method for preparing monoclonal antibodies, 0.02 mM, in phosphate buffer, pH7, 20 mM) and the reaction mixture was allowed to stay at 4° C. overnight;
(2) MC-VC-PAB-MMAE (commercially available from Lenena, biopharma, 0.12 mM) in DMA (commercially available from Aldrich Sigma) was introduced and the reaction was continued at 4° C. for 2 h;
(3) Cysteine (0.08 mM) was added to deplete excessive MC-VC-PAB-MMAE;
(4) EDTA (0.08 mM) was added to trap Zn2+ and DHAA (commercially available from Aldrich Sigma, 0.16 mM) was added to oxidize the excessive thiol groups;
(5) the reaction mixture was subjected to purification using a de-salting column (type: 40K, 0.5 mL, REF: 87766, Lot #SJ251704, Manufacturer: Thermo).

As a control, the reaction is performed in the same steps in the presence of 0.05 mM TCEP but without $ZnCl_2$.

Homogeneity assays. Finally, the drug/antibody ratio (DAR) and product distribution were analyzed using HIC-HPLC. Purification of D0, D2, D4, D6 and D8 by hydrophobic interaction chromatography (HIC) was performed on a Toyopearl phenyl 650M HIC column (Tosoh Biosciences, Montgomeryville, PA) at a flow rate of 10 m/min at ambient temperature. The column size was 1 mL per 7.5 mg of ADCs. Solvent A was 2.0 M NaCl and 50 mM sodium phosphate pH 7. Solvent B was 80% v/v 50 mM sodium phosphate pH 7 and 20% v/v acetonitrile. The column was previously equilibrated with 5 column volumes of solvent A. the ADCs were mixed with 0.67 volume of 5 M NaCl (2.0 M final) and applied to the column. D0 was not retained by the column. The different drug loaded species were eluted by sequential step gradients: D2 was eluted with 35% solvent B, D4 was eluted with 70% solvent B, D6 was eluted with 95% solvent B, and D8 was eluted with 100% solvent B.

The results were shown in Table 2 and FIG. 3-4.

TABLE 2

| Sample Name | D0 (wt %) | D2 (wt %) | D4 (wt %) | D6 (wt %) | D8 (wt %) | HIC-DAR |
|---|---|---|---|---|---|---|
| Rituxan-MMAE (with $ZnCl_2$, FIG. 3) | 1.4 | 12.6 | 75.0 | 6.1 | 4.9 | 4.0 |
| Rituxan-MMAE (without $ZnCl_2$, ) FIG. 4 | 4.6 | 24.4 | 38.4 | 24.1 | 8.5 | 4.2 |

Example 3. Preparation of Erbitux-MC-VC-PAB-MMAE Conjugate by Using the Process of the Present Disclosure and Homogeneity Thereof The Erbitux-MC-VC-PAB-MMAE conjugate is prepared in a one-pot reaction:
(1) $ZnCl_2$ (0.04 mM) and TCEP (0.08 mM) were subsequently added to a solution of Erbitux (produced in WuXi Biologics, according to the published corresponding protein sequences, via standard method for preparing monoclonal antibodies, 0.02 mM, in phosphate buffer, pH7, 20 mM and the reaction mixture was allowed to stay at 4° C. overnight;

(2) MC-VC-PAB-MMAE (commercially available from Lenena, biopharma, 0.12 mM) in DMA (commercially available from Aldrich Sigma) was introduced and the reaction was continued for 2 h at 4° C.;
(3) cysteine (0.08 mM) was added to deplete excessive MC-VC-PAB-MMAE;
(4) EDTA (0.08 mM) was added to trap $Zn^{2+}$ and DHAA (commercially available from Aldrich Sigma, 0.16 mM) was added to oxidize the excessive thiol groups;
(5) the reaction mixture was subjected to purification using a de-salting column (type: 40K, 0.5 mL, REF: 87766, Lot #SJ251704, Manufacturer: Thermo).

As a control, the reaction is performed in the same steps in the presence of 0.05 mM TCEP but without $ZnCl_2$.

Homogeneity assays. Finally, the drug/antibody ratio (DAR) and product distribution were analyzed using HIC-HPLC. Purification of D0, D2, D4, D6 and D8 by hydrophobic interaction chromatography (HIC) was performed on a Toyopearl phenyl 650M HIC column (Tosoh Biosciences, Montgomeryville, PA) at a flow rate of 10 m/min at ambient temperature. The column size was 1 mL per 7.5 mg of ADCs. Solvent A was 2.0 M NaCl and 50 mM sodium phosphate pH 7. Solvent B was 80% v/v 50 mM sodium phosphate pH 7 and 20% v/v acetonitrile. The column was previously equilibrated with 5 column volumes of solvent A. the ADCs were mixed with 0.67 volume of 5 M NaCl (2.0 M final) and applied to the column. D0 was not retained by the column. The different drug loaded species were eluted by sequential step gradients: D2 was eluted with 35% solvent B, D4 was eluted with 70% solvent B, D6 was eluted with 95% solvent B, and D8 was eluted with 100% solvent B.

The results were shown in Table 3 and FIG. 5-6.

TABLE 3

| Sample Name | D0 (wt %) | D2 (wt %) | D4 (wt %) | D6 (wt %) | D8 (wt %) | HIC-DAR |
|---|---|---|---|---|---|---|
| Erbitux-MMAE (with $ZnCl_2$, FIG. 5) | 1.6 | 9.8 | 77.9 | 6.5 | 4.2 | 4.0 |
| Erbitux-MMAE (without $ZnCl_2$, FIG. 6) | 8.1 | 28.5 | 35.5 | 21.0 | 6.8 | 3.8 |

As shown in Table 1-3 and FIGS. 1, 3 and 5, the results demonstrate that the content of D4 is generally more than 65 wt %, for example, more than 70 wt %, and more than 77 wt % (FIGS. 1, 3 and 5). In contrast, the content of D4 is normally less than 40 wt % in the ADCs prepared by control conjugation process without transitional metal ions (FIGS. 2, 4 and 6). These results clearly demonstrate that the ADC prepared with the process of the present disclosure by using transitional metal ions has a significantly improved homogeneity.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

What is claimed:

1. A method of preparing an antibody-drug conjugate (ADC), comprising the following steps:
   (a) incubating a reductant and an antibody in the presence of an effective amount of a transition metal ion in a buffer system to reduce inter-chain disulfide bonds within the antibody to generate reduced thiol groups; and
   (b) introducing an excess amount of payload having a reactive group to react with the reduced thiol groups resulted from step (a).

2. The method of claim 1, wherein the transition metal ion is $Zn^{2+}$, $Cd^{2+}$, $Hg^{2+}$, or a combination thereof.

3. The method of claim 2, wherein the transition metal ion is $Zn^{2+}$.

4. The method of claim 1, wherein the buffer system in step (a) is Hepes, Histidine buffer, phosphate-buffered saline (PBS), or 2-morpholinoethanesulphonic acid (MES), and the pH value of the buffer system is 5.5 to 8.

5. The method of claim 1, wherein the antibody in step (a) has a concentration of 0.01 to 0.1 mM.

6. The method of claim 1, wherein step (a) is performed at a temperature of −10° C. to 37° C.

7. The method of claim 1, wherein the reductant in step (a) is tris(2-carboxyethyl)phosphine (TCEP).

8. The method of claim 1, wherein the payload comprises a maleimide moiety, bromide, or iodide.

9. The method of claim 1, wherein the antibody is a monoclonal antibody or a polyclonal antibody.

10. The method of claim 1, wherein the antibody is a human antibody, a humanized antibody, a chimeric antibody or an antigen-binding moiety thereof.

11. The method of claim 1, wherein the antibody is an IgG1 or an IgG4.

12. The method of claim 1, wherein the payload comprises a diagnostic agent, a therapeutic agent or a labelling agent.

13. The method of claim 1, wherein the resultant ADC are classified into D0, D2, D4, D6 and D8 based on the ratio between the antibody and payload molecules in an ADC molecule, wherein D4 in the resultant ADC has a weight percentage of over 65% on the basis of total weight of D0, D2, D4, D6 and D8, wherein
   D0 refers to an antibody molecule that is not coupled to any payload molecules;
   D2 refers to an ADC molecule in which two payload molecules are coupled to an antibody molecule;
   D4 refers to an ADC molecule in which four payload molecules are coupled to an antibody molecule;
   D6 refers to an ADC molecule in which six payload molecules are coupled to an antibody molecule; and
   D8 refers to an ADC molecule in which eight payload molecules are coupled to an antibody molecule.

14. The method of claim 1, wherein the resultant ADC are classified into D0, D2, D4, D6 and D8 based on the ratio between the antibody and payload molecules in an ADC molecule, wherein D0 and D8 together in the resultant ADC have a weight percentage of less than 10%, and D6 has a weight percentage of less than 10% on the basis of total weight of D0, D2, D4, D6 and D8, wherein
   D0 refers to an antibody molecule that is not coupled to any payload molecules;
   D2 refers to an ADC molecule in which two payload molecules are coupled to an antibody molecule;
   D4 refers to an ADC molecule in which four payload molecules are coupled to an antibody molecule;

D6 refers to an ADC molecule in which six payload molecules are coupled to an antibody molecule; and D8 refers to an ADC molecule in which eight payload molecules are coupled to an antibody molecule.

15. The method of claim 1, wherein the payload selectively reacts with the reduced thiol groups in an Fab region of the antibody in step (b) in presence of the transition metal ion.

16. The method claim 6, wherein step (a) is performed at a temperature of 0° C. to 20° C.

17. A method of preparing a pharmaceutical composition, comprising the following steps: introducing an excess amount of payload having a reactive group to react with an antibody having one or more reduced thiol groups in presence of an effective amount of a transition metal ion; adding an effective amount of an oxidant to oxidize unreacted thiol groups; purifying the resultant antibody-drug conjugate; and preparing a pharmaceutical composition comprising the antibody-drug conjugate and a pharmaceutically acceptable carrier.

18. The method of claim 1, further comprising
   (c) adding an effective amount of an oxidant to oxidize unreacted thiol groups;
   (d) purifying the resultant antibody-drug conjugate; and
   (e) preparing a pharmaceutical composition comprising the antibody-drug conjugate and a pharmaceutically acceptable carrier.

19. The method of claim 18, wherein the oxidant in step (c) is dehydroascorbic acid (DHAA).

* * * * *

UNITED STATES PATENT AND TRADEMARK OFFICE
CERTIFICATE OF CORRECTION

| | | |
|---|---|---|
| PATENT NO. | : 12,109,273 B2 | |
| APPLICATION NO. | : 17/410574 | |
| DATED | : October 8, 2024 | |
| INVENTOR(S) | : Ao Ji, Chuchu Sun and Wenxu He | |

It is certified that error appears in the above-identified patent and that said Letters Patent is hereby corrected as shown below:

In the Claims

In Claim 13, Column 46, Line 43, delete "DO," and insert -- D0, --.

In Claim 16, Column 47, Line 9, after "method" insert -- of --.

Signed and Sealed this
Third Day of December, 2024

Katherine Kelly Vidal
*Director of the United States Patent and Trademark Office*